United States Patent [19]

Bundy

[11] 4,097,489

[45] Jun. 27, 1978

[54] 9-DEOXY-9α,6-NITRILO OR 6,9α-IMINO-PGF COMPOUNDS

[75] Inventor: Gordon L. Bundy, Portage, Mich.

[73] Assignee: The Upjohn Company, Kalamazoo, Mich.

[21] Appl. No.: 807,514

[22] Filed: Jun. 17, 1977

[51] Int. Cl.$^2$ .............................................. C07D 209/52
[52] U.S. Cl. ........................ 260/326.27; 260/293.56; 260/293.61; 260/295 F; 260/295 K; 260/376.25; 424/248.54; 424/248.55; 424/250; 424/263; 424/267; 424/274; 544/143; 544/144; 544/362; 544/373; 544/364; 542/426; 542/429; 542/430; 542/431
[58] Field of Search ................................... 260/326.27

[56] References Cited

U.S. PATENT DOCUMENTS

| 3,931,289 | 1/1976 | Bundy | 260/473 A |
|---|---|---|---|
| 3,983,157 | 9/1976 | Bundy | 260/473 A |
| 3,983,158 | 9/1976 | Bundy | 260/473 A |

FOREIGN PATENT DOCUMENTS 2,535,693  3/1976  Germany ........................ 260/473 A

OTHER PUBLICATIONS

Johnson et al., Prostaglandins, vol. 12, p. 915 (1976).

*Primary Examiner*—Donald G. Daus
*Assistant Examiner*—Mary Vaughn
*Attorney, Agent, or Firm*—Robert A. Armitage

[57] ABSTRACT

This invention relates to certain structural and pharmacological analogs of prostacyclin ($PGI_2$) wherein a nitrogen atom is substituted for the 6,9α-epoxy-oxygen of prostacyclin. These novel nitrogen-containing prostacyclin-type compounds are useful for the pharmacological purposes for which prostacyclin is used, e.g., as antithrombotic agents, smooth muscle stimulators, gastric antisecretory agents, antihypertensive agents, antiasthma agents, nasal decongestants, or regulators of fertility and procreation.

52 Claims, No Drawings

9-DEOXY-9α,6-NITRILO OR 6,9α-IMINO-PGF COMPOUNDS

BACKGROUND OF THE INVENTION

This invention relates to novel structural and pharmacological analogs of prostacyclin (PGI$_2$). In particular, the present invention relates to prostacyclin-type compounds wherein the 6,9α-epoxy-oxygen atom of prostacyclin is replaced by a nitrogen atom.

Prostacyclin is an endogenously produced compound in mammalian species, being structurally and biosynthetically related to the prostaglandins (PG's). In particular, prostacyclin exhibits the following structure and atom numbering:

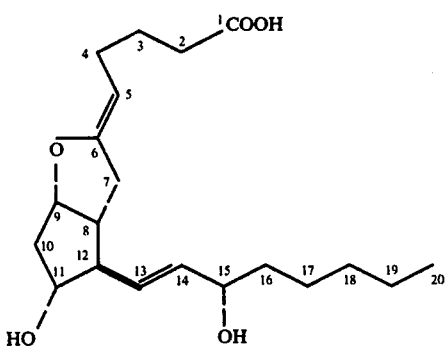

As is apparent from inspection of formula I, prostacyclin bears a structural relationship to PGF$_2$α, which exhibits the following structure and atom numbering:

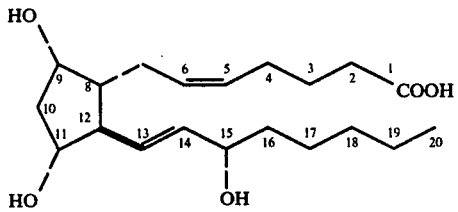

As is apparent by reference to formula II, prostacyclin may be trivially named as a derivative of PGF-type compounds. Accordingly, prostacyclin is trivially named 9-deoxy-6,9α-epoxy-(5Z)-5,6,-didehydro-PGF$_1$. For description of the geometric stereoisomerism employed above, see Blackwood et al., Journal of the American Chemical Society 90, 509 (1968). Further for a description of prostacyclin and its structural identification, see Johnson et al. Prostaglandins 12, 915 (1976).

For convenience, the novel prostacyclin analogs described herein will be referred to by the trivial, art-recognized system of nomenclature described by N. A. Nelson, Journal of Medicinal Chemistry, 17, 911 (1974) for the prostaglandins. Accordingly, all of the novel prostacyclin derivatives herein will be named as 9-deoxy-PGF$_1$-type compounds.

In formulas I and II above, as well as in formulas hereinafter, broken line attachments to any ring indicate substituents in "alpha" (α) configuration i.e., below the plane of such ring. Heavy solid line attachments to any ring indicate substituents in "beta" (β) configuration, i.e., above the plane of such ring. The use of wavy lines (∼) herein will represent attachment of substituents in either the alpha or beta configuration or attachment in a mixture of alpha and beta configurations.

The side-chain hydroxy at C-15 in the above formulas is in S or R configuration, as determined by the Cahn-Ingold-Prelog sequence rules. See J. Chem. Ed. 41:16 (1964). See, also Nature 212, 38 (1966) for discussion of the stereochemistry of the prostaglandins, which discussion applies to the novel prostacyclin analogs herein. Expressions such as C-2, C-15, and the like, refer to the carbon atom in the prostaglandin or prostacyclin analog which is in the position corresponding to the position of the same number in PGF$_2$α or prostacyclin, as enumerated above.

Molecules of prostacyclin and the novel, asymmetric prostacyclin analogs each have several centers of asymmetry, and can exist in racemic (optically inactive) form and in either of the two enantiomeric (optically active) forms, i.e., the dextrorotatory and levorotatory forms. As drawn, the above formula for prostacyclin corresponds to that endogenously produced in mammalian tissues. In particular, refer to the stereoconfiguration at C-8 (alpha), C-9 (alpha), C-11 (alpha), and C-12 (beta) of endogenously-produced prostacyclin. The mirror image of the above formula for prostacyclin represents the other enantiomer. The racemic forms of prostacyclin contains equal numbers of both enantiomeric molecules, and the above formula I and its mirror image is needed to represent correctly the corresponding racemic prostacyclin.

For convenience hereinafter, use of the term prostaglandin ("PG") or prostacyclin ("PGI$_2$") will mean the optically active form of that prostaglandin or prostacyclin thereby referred to with the same absolute configuration as PGF$_2$α, obtained from mammalian tissues.

The term "prostaglandin-type" or "prostacyclin-type" (PG-type or PGI-type) product, as used herein, refers to any monocyclic or bicyclic cyclopentane derivative herein which is useful for at least one of the same pharmacological purposes as the prostaglandins or prostacyclin, respectively.

The formulas as drawn herein, which depict a prostaglandin-type or prostacyclin-type product or an intermediate useful in their respective preparations, each represent the particular stereoisomer of the prostaglandin-type or prostacyclin-type product which is of the same relative stereochemical configuration as a corresponding prostaglandin or prostacyclin obtained from mammalian tissues, or the particular stereoisomer of the intermediate which is useful in preparing the above stereoisomer of the prostaglandin-type or prostacyclin-type products.

The term "prostacyclin analog", as used herein, represents that stereoisomer of a prostacyclin-type product which is of the same relative stereochemical configuration as prostacyclin obtained from mammalian tissues or a mixture comprising that stereoisomer and the enantiomer thereof. In particular, where a formula is used to depict a prostacyclin-type product herein, the term "prostacyclin analog" refers to the compound of that formula or a mixture comprising that compound and the enantiomer thereof.

SUMMARY OF THE INVENTION

The present invention particularly comprises:
A prostacyclin analog of the formula

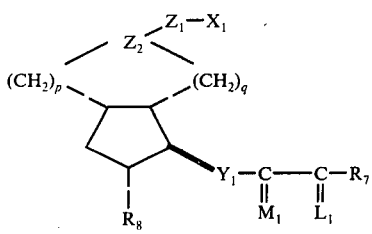 III wherein $Z_2$ is

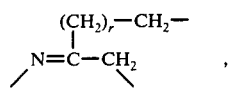 (1)

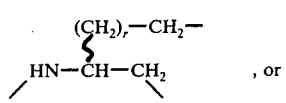 , or (2)

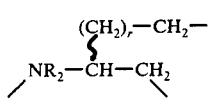 (3)

wherein
  $R_2$ is alkyl of one to 4 carbon atoms, inclusive, or alkylcarbonyl of one to 4 carbon atoms, inclusive;
  wherein one of $p$, $q$, and $r$ is the integer one and the other two are the integer zero;
  wherein $Z_1$ is
    (1) $-(CH_2)_g-CH_2-CH_2-$,
    (2) $-(CH_2)_g-CH_2-CF_2-$, or
    (3) trans$-(CH_2)_g-CH=CH-$,
  wherein $g$ is the integer zero, one, or 2;
  wherein $R_8$ is hydrogen, hydroxy, or hydroxymethyl;
  wherein $Y_1$ is
    (1) trans$-CH=CH-$,
    (2) cis$-CH=CH-$,
    (3) $-CH_2CH_2-$,
    (4) trans$-CH=C(Hal)-$, or
    (5) $-C\equiv C-$
  wherein Hal is chloro or bromo;
  wherein
    $M_1$ is

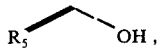
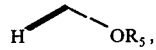
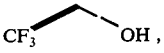
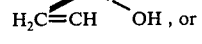

wherein
  $R_5$ is hydrogen or alkyl with one to 4 carbon atoms, inclusive.
  wherein $L_1$ is

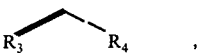

 , or a mixture of

and

wherein $R_3$ and $R_4$ are hydrogen, methyl, or fluoro, being the same or different, with the proviso that one of $R_3$ and $R_4$ is fluoro only when the other is hydrogen or fluoro;
  wherein $X_1$ is
    (1) $-COOR_1$ wherein $R_1$ is hydrogen; alkyl of one to 12 carbon atoms, inclusive; cycloalkyl of 3 to 10 carbon atoms, inclusive, aralkyl of 7 to 12 carbon atoms, inclusive; phenyl; phenyl substituted with one, two, or three chloro or alkyl of one to 3 carbon atoms; phenyl substituted in the para position by

 (a)

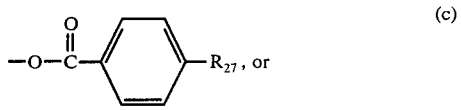 (b)

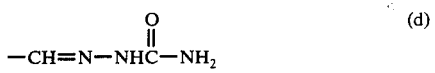 (c)

$-CH=N-NHC(O)-NH_2$ (d)

wherein $R_{25}$ is methyl, phenyl, acetamidophenyl, benzamidophenyl, or $-NH_2$; $R_{26}$ is methyl, phenyl, $-NH_2$, or methoxy; and $R_{27}$ is hydrogen or acetamido; inclusive, or a pharmacologically acceptable cation;
    (2) $-CH_2OH$; or
    (3) $-COL_4$, wherein $L_4$ is
      (a) amido of the formula $-NR_{21}R_{22}$, wherein $R_{21}$ and $R_{22}$ are hydrogen; alkyl of one to 12 carbon atoms, inclusive; cycloalkyl of 3 to 10 carbon atoms, inclusive; aralkyl of 7 to 12 carbon atoms, inclusive; phenyl; phenyl substituted with one, 2, or 3 chloro, alkyl of one to 3 carbon atoms, inclusive;
      hydroxy, carboxy, alkoxycarbonyl of one to 4 carbon atoms, inclusive, or nitro; carboxyalkyl of one to four carbon atoms, inclusive; carbamoylalkyl of one to four carbon atoms, inclusive; cyanoalkyl of one to four carbon atoms, inclusive; acetylalkyl of one to four carbon atoms, inclusive; benzoylalkyl of one to four carbon atoms, inclusive; benzoylalkyl substituted by one, 2, or 3 chloro, alkyl of one to 3 carbon atoms inclusive; hydroxy, alkoxy of one to 3 carbon atoms, inclusive;

carboxy, alkoxycarbonyl of one to 4 carbon atoms, inclusive; or nitro; pyridyl; pyridyl substituted by one, 2, or 3 chloro, alkyl of one to 3 carbon atoms, inclusive; or alkoxy of one to 3 carbon atoms, inclusive; pyridylalkyl of one to 4 carbon atoms, inclusive; pyridylalkyl of one to 4 carbon atoms, inclusive; pyridylalkyl substituted by one, 2, or 3 chloro, alkyl of one to 3 carbon atoms, inclusive; hydroxy, alkoxy of one to 3 carbon atoms, inclusive; hydroxyalkyl of one to 4 carbon atoms, inclusive; dihydroxyalkyl of one to 4 carbon atoms, and trihydroxyalkyl of one to 4 carbon atoms; with the further proviso that not more than one of $R_{21}$ and $R_{22}$ is other than hydrogen or alkyl;

(b) cycloamido selected from the group consisting of

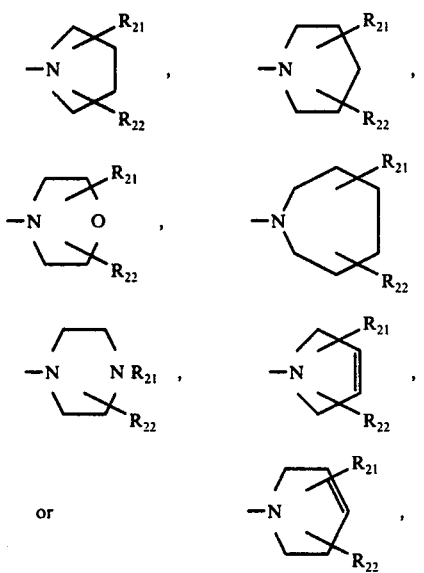

wherein $R_{21}$ and $R_{22}$ are as defined above;

(c) carbonylamido of the formula —$NR_{23}COR_{21}$, wherein $R_{23}$ is hydrogen or alkyl of one to 4 carbon atoms and $R_{21}$ is as defined above;

(d) sulphonylamido of the formula —$NR_{23}$-$SO_2R_{21}$, wherein $R_{21}$ and $R_{23}$ are as defined above; or (e) hydrazino of the formula —$NR_{23}R_{24}$, wherein $R_{24}$ is amido of the formula —$NR_{21}R_{22}$, as defined above, or cycloamido, as defined above;

wherein $R_7$ is

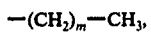 (1)

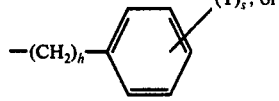 (2)

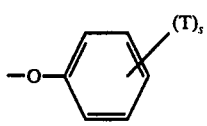 (3)

wherein $m$ is the integer one to 5, inclusive, $h$ is the integer zero to 3, inclusive; $s$ is the integer zero, one, 2, or 3, and T is chloro, fluoro, trifluoromethyl, alkyl of one to 3 carbon atoms, inclusive, or alkoxy of one to 3 carbon atoms, inclusive, with the proviso that not more than two T's are other than alkyl: and the pharmacologically acceptable acid addition salts thereof when $R_2$ is not alkylcarbonyl and $R_1$ is not a pharmacologically acceptable cation.

For the novel compounds herein where $Z_1$ is —$(CH_2)_g$—$CH_2$—$CF_2$—, such compounds are referred to herein as 2,2-difluoro-PG-type compounds. Further, compounds herein wherein $Z_1$ is trans-$(CH_2)_g$—CH=•CH— are named as trans-2,3-didehydro-PG-type compounds.

When $p$ is zero and $g$ is one or 2, the compounds described herein are additionally named as 2a-homo-PG-type or 2a,2b-dihomo-PG-type compounds, respectively. In this event the additional methylene or ethylene group is considered for the purposes of nomenclature as though it were inserted between the carbon atoms C-2 and C-3. Further, such additional carbon atoms are denoted as C-2a and C-2b, counting from the C-2 to the C-3 carbon atoms, respectively.

When $p$ is one and $g$ is zero or 2, the novel compounds herein are further designated as 2-nor-PG-type or 2a-homo-PG-type compounds. In the former case, the methylene group at C-2 is considered to have been deleted, thereby resulting in the attachment of the carbon atom at C-1 to C-3. In the latter case, the rationale for the nomenclature is as described above for compounds wherein $p$ is zero and $g$ is one.

The novel prostacyclin analogs herein wherein $R_8$ is hydrogen or hydroxymethyl are respectively referred to as 11-deoxy-PG-type or 11-deoxy-11-hydroxymethyl-PG-type compounds. Additionally, when $Y_1$ is cis—CH=CH—, —$CH_2CH_2$—, trans-CH=C(Hal)-, or —C≡C—, the novel compounds thereby referred to are named as 13-cis-PG-type, 13,14-dihydro-PG-type, 14-halo-PG-type, or 13,14-didehydro-PG-type, compounds.

Compounds herein wherein $M_1$ is

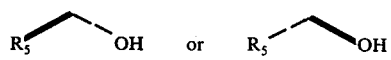

and $R_5$ is alkyl are referred to as 15-alkyl-PG-type compounds. When $M_1$ is

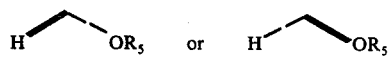

and $R_5$ is alkyl, the novel compounds herein thusly described are named as PG-type, 15-alkyl ethers. Compounds herein wherein $M_1$ is

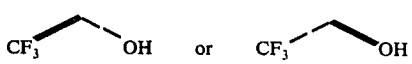

are referred to as 15-trifluoromethyl-PG-type compounds. Further, compounds herein wherein $M_1$ is

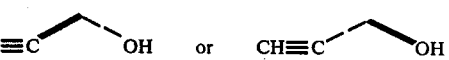

are named as 15-ethynyl-PG-type compounds. Finally, compounds herein wherein $M_1$ is

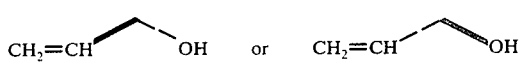

are named as 15-ethenyl-PG-type compounds.

With the exception of the 13-cis-PG-type compounds described above, all the above compounds exhibiting a hydroxy or alkoxy moiety in the beta configuration at C-15 are additionally referred to as 15-epi-PG-type compounds. For the 13-cis-PG-type compounds herein, only compounds exhibiting the hydroxy or alkoxy moiety in the alpha configuration at C-15 are referred to as 15-epi-PG-type compounds. The rationale for this system of nomenclature with respect to the natural and epimeric configurations at C-15 is described in U.S. Pat. No. 4,016,184, issued April 5, 1977.

When $R_7$ is $-(CH_2)_m-CH_3$, wherein $m$ is as defined above, the novel compounds herein are named as 19,20-dinor-PG-type, 20-nor-PG-type, 20-methyl-PG-type or 20-ethyl-PG-type compounds when $m$ is one, 2, 4, or 5, respectively.

When $R_7$ is

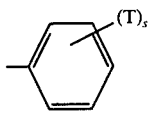

wherein T and $s$ are as defined above, and neither $R_3$ nor $R_4$ is methyl, the novel compounds herein are named as 16-phenyl-17,18,19,20-tetranor-PG-type compounds, when $s$ is zero. When $s$ is one, 2, or 3, the corresponding compounds are named as 16-(substituted phenyl)-17,18,19,20-tetranor-PG-type compounds. When one and only one of $R_3$ and $R_4$ is methyl or both $R_3$ and $R_4$ are methyl, then the corresponding compounds wherein $R_7$ is as defined in this paragraph are named as 16-phenyl- or 16-(substituted phenyl-18,19,20-trinor-PG-type; or 16-methyl-16-phenyl- or 16-methyl- or 16-(substituted phenyl)-18,19,20-trinor-PG-type compounds, respectively.

When $R_7$ is

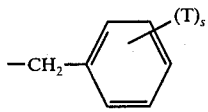

wherein T and $s$ are as defined above, the novel compounds herein are named as 17-phenyl-18,19,20-trinor-PG-type compounds, when $s$ is 0. When $s$ is one, 2, or 3, the corresponding compounds are named as 17-(substituted phenyl)-18,19,20-trinor-PG-type compounds.

When $R_7$ is

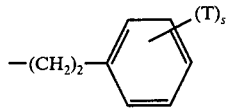

wherein T and $s$ are as defined above, the novel compounds herein are named as 18-phenyl-19,20-dinor-PG-type compounds. when $s$ is 0. When $s$ is one, 2, or 3, the corresponding compounds are named as 18-(substituted phenyl)-19,20-dinor-PG-type compounds.

When $R_7$ is

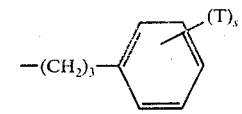

wherein T and $s$ are as defined above, the novel compounds herein are named as 19-phenyl-20-nor-PG-type compounds, when $s$ is 0. When $s$ is one, 2, or 3, the corresponding compounds are named as 19-(substituted phenyl)-20-nor-PG-type compounds.

When $R_7$ is

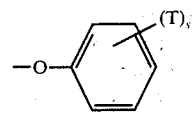

wherein T and $s$ are as defined above, and neither $R_3$ nor $R_4$ is methyl, the novel compounds herein are named as 16-phenoxy-17,18,19,20-tetranor-PG-type compounds, when $s$ is zero. When $s$ is one, 2, or 3, the corresponding compounds are named as 16-(substituted phenoxy)-17,18,19,20-tetranor-PG-type compounds. When one and only one of $R_3$ and $R_4$ is methyl or both $R_3$ and $R_4$ are methyl, then the corresponding compounds wherein $R_7$ is as defined in this paragraph are named as 16-phenoxy- or 16-(substituted phenoxy)-18,19,20-trinor-PG-type compounds or 16-methyl-16-phenoxy- or 16-substituted phenoxy)-18,19,20-trinor-PG-type compounds, respectively.

When at least one of $R_3$ and $R_4$ is not hydrogen then (except for the 16-phenoxy or 16-phenyl compounds discussed above), there are thusly described the 16-methyl-PG-type (one and only one of $R_3$ and $R_4$ is methyl), 16,16-dimethyl-PG-type ($R_3$ and $R_4$ are both methyl), 16-fluoro-PG-type (one and only one of $R_3$ and $R_4$ is fluoro), and 16,16-difluoro-PG-type ($R_3$ and $R_4$ are both fluoro) compounds. For those compounds wherein $R_3$ and $R_4$ are different, the prostaglandin analogs so represented contain an asymmetric carbon atom at C-16. Accordingly, two epimeric configurations are possible: "(16S)" and "(16R)". Further, there is described by this invention the C-16 epimeric mixture: "(16RS)".

When $X_1$ is $-CH_2OH$, the novel compounds herein are named as 2-decarboxy-2-hydroxymethyl-PG-type compounds.

Then $X_1$ is $-COL_4$ the novel compounds herein are named as PG-type, amides. Further when $X_1$ is —COOR, the novel compounds herein are named as PG-type, esters and PG-type, salts when $R_1$ is not hydrogen.

Finally, the NOMENCLATURE TABLE herein describes the convention by which trivial names are further assigned for the novel compounds herein:

NOMENCLATURE TABLE

| | $Z_2$ | p | q | Compound type |
|---|---|---|---|---|
| (1) | $(CH_2)_r-CH_2-$<br>$N=C-CH_2$ | 0 | 0 | 9-deoxy-9α,6-nitrilo-PGF$_1$-type compounds |
| | | 0 | 1 | 9-deoxy-9α,5-nitrilo-PGF$_1$-type compounds |
| | | 1 | 0 | 9-deoxy-6,9α-nitrilo-methylene-PGF$_1$-type compounds |
| (2) | $(CH_2)_r-CH_2-$<br>$NH-CH-CH_2$ | 0 | 0 | 6R- or 6S- 9-deoxy-6,9α-imino-PGF$_1$-type compounds |
| | | 0 | 1 | 5R- or 5S- 9-deoxy-5,9α-imino-PGF$_1$-type compounds |

NOMENCLATURE TABLE-continued

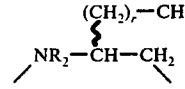

| | | p | q | Compound type |
|---|---|---|---|---|
| | | 1 | 0 | 6R- or 6S- 9-deoxy-6,9α-iminomethylene-PGF$_1$-type compounds |
| (3) | (CH$_2$)$_p$—CH$_2$— | 0 | 0 | 6R- or 6S-N-alkyl- or N-acyl-9-deoxy-6,9α-imino PGF$_1$-type compounds |
| | NR$_2$—CH—CH$_2$ | 0 | 1 | 5R- or 5S-N-alkyl- or N-acyl-9-deoxy-5,9α-imino PGF$_1$-type compounds |
| | | 1 | 0 | 6R- or 6S-N-alkyl- or N-acyl-9-deoxy-6,9α-iminomethylene-PGF$_1$-type compounds |

Examples of alkyl of one to 12 carbon atoms, inclusive, are methyl, ethyl, propyl, butyl, pentyl, hexyl, heptyl, octyl, nonyl, decyl, undecyl, dodecyl, and isomeric forms thereof.

Examples of cycloalkyl of 3 to 10 carbon atoms, inclusive, which includes alkyl-substituted cycloalkyl, are cyclopropyl, 2-methylcyclopropyl, 2,2-dimethylcyclopropyl, 2,3-diethylcyclopropyl, 2-butylcyclopropyl, cyclobutyl, 2-methylcyclobutyl, 3-propylcyclobutyl, 2,3,4-triethylcyclobutyl, cyclopenyl, 2,2-dimethylcyclopentyl, 2-pentylcyclopentyl, 3-tert-butylcyclopentyl, cycohexyl, 4-tert-butylcyclohexyl, 3-isopropylcyclohexyl, 2,2-dimethylcyclohexyl, cycloheptyl, cyclooctyl, cyclononyl, and cyclodecyl.

Examples of aralkyl of 7 to 12 carbon atoms, inculsive, are benzyl, 2-phenethyl, 1-phenylethyl, 2-phenylpropyl, 4-phenylbutyl, 3phenylbutyl, 2-(1-naphthylethyl), and 1-(2-naphthylmethyl).

Examples of phenyl substituted by one to 3 chloro or alkyl of one to 4 carbon atoms, inclusive, are p-chlorophenyl, m-chlorophenyl, 2,4-dichlorophenyl, 2,4,6-trichlorophenyl, p-tolyl, m-tolyl, o-tylyl, p-ethylphenyl, p-tert-butylphenyl, 2,5-dimethylphenyl, 4-chloro-2-methylphenyl, and 2,4-dichloro-3-methylphenyl. Examples of

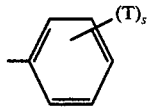

wherein T is alkyl of one to 3 carbon atoms, inclusive, fluoro, chloro, trifluoromethyl, or alkoxy of one to 3 carbon atoms, inclusive; and s is zero, one, 2, or 3, with the proviso that not more than two T's are other than alkyl, are phenyl, (o-, m-, or p-)tolyl, (o-, m-, or p-)ethylphenyl, 2-ethyl-p-tolyl, 4-ethyl-o-tolyl, 5-ethyl-m-tolyl, (o-, m-, or p-)propylphenyl, 2-propyl-(o-, m-, or p-)tolyl, 4-isopropyl-2,6-xylyl, 3-propyl-4-ethylphenyl, (2,3,4-, 2,3,5-, 2,3,6-, or 2,4,5-trimethylphenyl, (o-, m-, p-)fluorophenyl, 2-fluoro-(o, m-, or p-)tolyl, 4-fluoro-2,5-xylyl, (2,4-, 2,5-, 2,6- 3,4-, or 3,5-)difluorophenyl, (o-, m-, or p-)chlorophenyl, 2-chloro-p-tolyl, (3-, 4-, 5-, or 6-)chloro-o-tolyl, 4-chloro-2propylphenyl, 2-isopropyl-4-chlorophenyl, 4-chloro-3,5-xylyl, (2,3-, 2,4-, 2,5-, 2,6-, 3,4-, or 3,5-(dichlorophenyl), 4-chloro-3-fluorophenyl, (3-, or 4-(chloro-2-fluorophenyl, o-, m-, or p-trifluoromethylphenyl, (o-, m-, or p-methoxyphenyl, (o-, m-, or p-)ethoxyphenyl, (4- or 5-)chloro-2-methoxyphenyl, and 2,4-dichloro(5- or 6-)methylphenyl.

Examples of phenyl esters substituted in the para position (i.e. X$_1$ is —COOR$_1$, R$_1$ is p-substituted phenyl) include p-acetamidophenyl ester, p-benzamidophenyl ester, p-(p-acetamidobenzamido)phenyl ester, p-(p-benzamidobenzamido)phenyl ester, p-amidocarbonylamidophenyl ester, p-acetylphenyl ester, p-benzylphenyl ester, p-amidocarbonylphenyl ester, p-methoxycarbonylphenyl ester, p-benzoyloxyphenyl ester, p-(p-acetamidobenzoyloxy)phenyl ester, and p-hydroxybenzaldehyde semicarbazone ester.

Examples of novel prostacyclin amides herein (i.e. X$_1$ is COL$_4$) include the following:

(1) Amides within the scope of alkylamido groups of the formula —NR$_{21}$R$_{22}$ are methylamide, ethylamide, n-propylamide, n-butylamide, n-pentylamide, n-hexylamide, n-heptylamide, n-octylamide, n-nonylamide, n-decylamide, n-undecylamide and n-dodecylamide, and isomeric forms thereof. Further examples are dimethylamide, diethylamide, di-n-propylamide, di-n-butylamide, methylethylamide, methylpropylamide, methylbutylamide, ethylpropylamide, ethylbutylamide, and propylbutylamide. Amides within the scope of cycloalkylamido are cyclopropylamide, cyclobutylamide, cyclopentylamide, 2,3-dimethylcyclopentylamide, 2,2-dimethylcyclopentylamide, 2-methylcyclopentylamide, 3-tert-butylcyclopentylamide, cyclohexylamide, 4-tert-butylcyclohexylamide, 3-isopropylcyclohexylamide, 2,2-dimethylcyclohexylamide, cycloheptylamide, cyclooctylamide, cyclononylamide, cyclodecylamide, N-methyl-N-cyclobutylamide, N-methyl-N-cyclopentylamide, N-methyl-N-cyclohexylamide, N-ethyl-N-cyclopentylamide, N-ethyl-N-cyclohexylamide, dicyclopentylamide, and dicyclohexylamide. Amides within the scope of aralkylamido are benzylamide, 2-phenylethylamide, 2-phenylethylamide, N-methyl-N-benzylamide, and dibenzylamide. Amides within the scope of substituted phenylamido are p-chloroanilide, m-chloroanilide, 2,4-dichloroanilide, 2,4,6-trichloroanilide, m-nitroanilide, p-nitroanilide, p-methoxyanalide, 3,4-dimethoxyanilide, 3,4,5-trimethoxyanilide, p-hydroxymethylanilide, p-methylanalide, m-methylanilide, p-ethylanilide, t-butylanilide, p-carboxyanilide, p-metoxycarbonylanilide, o-carboxyanilide and o-hydroxyanilide. Amides within the scope of carboxyakylamido are carboxymethylamide. carboxyethylamide, carboxypropylamide, and carboxybutylamide. Amides within the scope of carbamoylakylamido are carbamoylmethylamide, carbamoylethylamide, carbamoylpropylamide, and carbamoylbutylamide. Amides within the scope of cyanoalkylamido are cyanomethylamide, cyanoethylamide, cyanopropylamide, and cyanobutylamide. Amides within the scope of acetylalkylamido are acetylmethylamide, acetylethylamide, acetylpropylamide, and acetylbutylamide. Amides within the scope of benzoylalkylamido are benzoylmethylamide, benzoylethylamide, benzoylpropylamide, and benzoylbutylamide. Amides within the scope of substituted benzoylalkylamido are p-chlorobenzoylmethylamide, m-chlorobenzoylmethylamide, 2,4-dichlorobenzoylmethylamide, 2,4,6-trichlorobenzoylmethylamide, m-nitrobenzoylmethylamide, p-nitrobenzoylmethylamide, p-methoxybenzoylmethylamide, 2,4-dimethoxybenzoylmethylamide, 3,4,5-trimethoxybenzoylmethylamide, p-hydroxymethylbenzoylmethylamide, p-methylbenzoylmethylamide, m-methylbenzoylmethylamide, p-ethylbenzoylmethylamide, t-butylbenzoylmethylamide, p-carboxybenzoylmethylamide, m-methoxycarbonylbenzoylmethylamide, o-carboxybenzoylmethylamide, o-hydroxybenzoylmethylamide, p-chlorobenzoylethylamide, m-chlorobenzoylethylamide, 2,4-dichlorobenzoylethylamide, 2,4,6-trichlorobenzoylethylamide, m-nitrobenzoylethylamide, p-nitrobenzoylethylamide, p-methoxybenzoylethylamide, p-methoxybenzoylethylamide, 2,4-dimethoxybenzoylethylamide, 3,4,5-trimethoxybenzoylethylamide, p-hydroxymethylbenzoylethylamide, p-methylbenzoylethylamide, m-methylbenzoylethylamide, p-ethylbenzoylethylamide, t-butyl-benzoylethylamide, p-carboxybenzoylethylamide, m-methoxycarbonylbenzoylethylamide, o-carboxybenzoylethylamide, o-hydroxybenzoylethylamide, p-chlorobenzoylpropylamide, m-chlorobenzoylpropylamide, 2,4-dichlorobenzoylpropylamide, 2,4,6-trichlorobenzoylpropylamide, m-nitrobenzoylpropylamide, p-nitrobenzoylpropylamide, p-methoxybenzoylpropylamide, 2,4-dimethoxybenzoylpropylamide, 3,4,5-trimethoxybenzoylpropylamide, p-hydroxymethylbenzoylpropylamide, p-methylbenzoylpropylamide, m-methylbenzoylpropylamide, p-ethylbenzoylpropylamide, t-butylbenzoylpropylamide, p-carboxybenzoylpropylamide, m-methoxycarbonylbenzoylpropylamide, o-carboxybenzoylpropylamide, o-hydroxybenzoylpropylamide, p-chlorobenzoylbutylamide, m-chlorobenzoylbutylamide, 2,4-dichlorobenzoylbutylamide, 2,4,6-trichlorobenzoylbutylamide, m-nitrobenzoylmethylamide, p-nitrobenzoylbutylamide, p-methoxybenzoylbutylamide, 2,4-dimethoxybenzoylbutylamide, 3,4,5-trimethoxybenzoylbutylamide, p-hydroxymethylbenzoylbutylamide, p-methylbenzoylbutylamide, m-methylbenzoylbutylamide, p-ethylbenzoylbutylamide, t-butylbenzoylbutylamide, p-carboxybenzoylbutylamide, m-methoxycarbonylbenzoylbutylamide, o-carboxybenzoylbutylamide, o-hydroxybenzoylmethylamide. Amides within the scope of pryidylamido are α-pyridylamide, β-pryidylamide, and γ-pryidylamide. Amides within the scope of substituted pyridylamido are 4-methyl-α-pyridylamide, 4-methyl-β-pyridylamide, 4-chloro-α-pyridylamide, and 4-chloro-β-pyridylamide. Amides within the scope of pyridylalkylamido are α-pyridylmethylamide, β-pyridylmethylamide, γ-pyridylmethylamide, α-pyridylethylamide, β-pyridylethylamide, γ-pyridylethylamide, α-pyridylpropylamide, β-pyridylpropylamide, γ-pyridylpropylamide, α-pyridylbutylamide, β-pyridylbutylamide, and γ-pyridylbutylamide. Amides within the scope of substituted pyridylalkylamido are 4-methyl-α-pyridylmethylamide, 4-methyl-β-pyridylmethylamide, 4-chloropyridylmethylamide, 4-chloro-β-pyridylmethylamide, 4-methyl-α-pyridylethylamide, 4-methyl-β-pyridylethylamide, 4-chloropyridylethylamide, 4-chloro-β-pyridylethylamide, 4-methyl-α-pyridylpropylamide, 4-methyl-β-pyridylpropylamide, 4-chloro-pyridylpropylamide, 4-chloro-β-pyridylpropylamide, 4-methyl-β-pyridylbutylamide, 4-methyl-α-pyridylbutylamide, 4-chloropyridylbutylamide, 4-chloro-β-pyridylbutylamide, 4-methyl-β-pyridylbutylamide. Amides within the scope of hydroxyalkyl are hydroxymethylamide, α-hydroxyethylamide, β-hydroxyethylamide, α-hydroxypropylamide, β-hydroxypropylamide, γ-hydroxypropylamide, 1-(hydroxymethyl)ethylamide, 1-(hydroxymethyl)propylamide, (2-hydroxymethyl)propylamide, and α,α-dimethyl-β-hydroxyethylamide. Amides within the scope of dihydroxyalkylamido are dihydroxymethylamide, α,α-dihydroxyethylamide, α,β-dihydroxyethylamide, β,β-dihydroxyethylamide, α,α-dihydroxypropylamide, α,β-dihydroxypropylamide, α,γ-dihydroxypropylamide, β,β-dihydroxypropylamide, β,γ-dihydroxypropylamide, γ,γ-dihydroxypropylamide, 1-(hydroxymethyl)2-hydroxyethylamide, 1-(hydroxymethyl)-1-hydroxyethylamide, α,α-dihydroxybutylamide, α,β-dihydroxybutylamide, α,γ-dihydroxybutylamide, α,δ-dihydroxybutylamide, β,β-dihydroxybutylamide, α,γ-dihydroxybutylamide, β,δ-dihydroxybutylamide, γ,γ-dihydroxybutylamide, γ,δ-dihydroxybutylamide, δ,δ-dihydroxybutylamide, and 1,1-bis(hydroxymethyl)ethylamide. Amides within the scope of trihydroxyalkylamino are tris(hydroxymethyl)methylamide and 1,3-dihydroxy-2-hydroxymethylpropylamide.

(2) Amides within the scope of the cycloamido groups described above are pyrrolidylamide, piperidylamide, morpholinylamide, hexamethyleneiminylamide, piperazinylamide, pyrrolinylamide, and 3,4-didehydropiperidinylamide.

(3) Amides within the scope of carbonylamido of the formula $-NR_{23}COR_{21}$ are methylcarbonylamide, ethylcarbonylamide, phenylcarbonylamide, and benzylcarbonylamide. Amides within the scope of sulfonylamido of the formula $-NR_{23}SO_2R_{21}$ are methylsulfonylamide, ethylsulfonylamide, phenylsulfonylamide, p-tolylsulfonylamide, benzylsulfonylamide.

(4) Hydrazides within the scope of the above hydrazino groups are hydrazine, N-aminopiperidine, benzoylhydrazine, phenylhydrazine, N-aminomorpholine, 2-hydroxyethylhydrazine, methylhydrazine, 2,2,2-hydroxyethylhydrazine and p-carboxyphenylhydrazine.

The term "pharmacologically acceptable acid addition salt" refers to those known acid addition salts of amine-containing compounds which are relatively nontoxic and readily acceptable to the host animal. Especially preferred are those acid addition salts which facilitate pharmaceutical formulation (e.g., more readily crystalline, etc.) or are readily and easily available for use. In particular, examples of acids from which such salts may be prepared are hydrochloric acid, hydrobromic acid, sulphuric acid, phosphoric acid, and other acids such as tartaric acid, fumaric acid, maleic acid, methanesulfonic acid, and p-toluene sulfonic acid.

The term "pharmacologically acceptable cation" refers to those pharmacologically acceptable salts of the prostacyclin-type carboxylic acids ($X_1$ is $-COOH$) described above which are conventionally employed with prostaglandins. In particular, such pharmacologically acceptable salts include pharmacologically acceptable metal cations, amine cations, and quarternary amonium cations. Additionally, basic amino acids such as arginine and lysine are employed. Further, certain amine cations such as THAM [tris(hydroxymethyl)amino methyl] and adamanamine are especially useful for the present purposes. Additionally, U.S. Pat. No. 3,016,184, issued Apr. 5, 1977 (particularly column 29), describes salts which are likewise preferred for the present purposes.

The novel prostacyclin analogs disclosed herein produce a multiplicity of biological responses, rendering these compounds useful for a variety of pharmacological purposes. In particular, the biological responses include platelet aggregation inhibition, smooth muscle stimulation, blood pressure lowering, gastric secretion reduction, NOSAC (non-steroidal antiinflammatory compound)-induced lesion inhibition, bronchodilation, nasal decongestion, peripheral vascular circulatory improvement, reproduction and fertility control, renal blood flow alteration, dermatosis reversal, inflammation reduction, and intraocular pressure reduction.

Accordingly, the novel prostacyclin analogs of the present invention are used as agents in the study, prevention, control, and treatment of diseases, and other undesirable physiological conditions, in mammals, particularly humans, valuable domestic animals, pets, zoological specimens, and laboratory animals (e.g., mice, rats, rabbits and monkeys), as follows:

(a) Platelet Aggregation Inhibition.

The novel prostacyclin analogs herein are useful whenever it is desired to inhibit platelet aggregation, to reduce the adhesive character of platelets, or to remove or prevent the formation of thrombi in mammals, including man. For example, these compounds are useful in the treatment and prevention of myocardial infarcts, to treat and prevent post-operative thrombosis, to promote patency of vascular grafts following surgery, and to treat conditions such as atherosclerosis, arteriosclerosis, blood clotting defects due to lipemia, and other clinical conditions in which the underlying etiology is associated with lipid imbalance or hyperlipidemia. Other in vivo applications include geriatric patients to prevent cerebral ischemic attacks and long term prophylaxis following myocardial infarcts and strokes. For these purposes, these compounds are administered systemically, e.g., intravenously, subcutaneously, intramuscularly, and in the form of sterile implants for prolonged action. For rapid response, especially in emergency situations, the intravenous route of administration is preferred. Doses in the range about 0.01 to about 10 mg. per kg. of body weight per day are used, the exact dose depending on the age, weight, and condition of the patient or animal, and on the frequency and route of administration.

The preferred dosage form for these compounds is oral, although other non-parenteral routes(e.g., buccal, rectal, sublingual) are likewise employed in preference to parenteral routes. Oral dosage forms are conventionally formulated (tablets, capsules, et cetera) and administered 2 to 4 times daily. Doses in the range of about 0.05 to 100 mg./kg. of body weight per day are effective.

The addition of these compounds to whole blood provides in vitro applications such as, storage of whole blood to be used in heart-lung machines. Additionally whole blood containing these compounds can be circulated through organs, e.g. heart and kidneys, which have been removed from a donor prior to transplant. They are also useful in preparing platelet rich concentrates for use in treating thrombocytopenia, chemotherapy, and radiation therapy. In vitro applications utilize a dose of 0.001-1.0 μg/ml of whole blood.

(b) Smooth Muscle Stimulation

The novel prostacyclin analogs herein are extremely potent in causing stimulation of smooth muscle, and are also highly active in potentiating other known smooth muscle stimulators, for example, oxytocic agents, e.g., oxytocin, and the various ergot alkaloids including derivatives and analogs thereof. Therefore, they are useful in place of or in combination with less than usual amounts of these known smooth muscle stimulators, for example, to relieve the symptoms of paralytic ileus, or to control or prevent atonic uterine bleeding after abortion or delivery, to aid in expulsion of the placenta, and during the puerperium. For the latter purpose, the compound is administered by intravenous infusion immediately after abortion or delivery at a dose in the range about 0.01 to about 50 μg. per kg. of body weight per minute until the desired effect is obtained. Subsequent doses are given by intravenous, subcutaneous, or intramuscular injection or infusion during puerperium in the range 0.01 to 2 mg. per kg. of body weight per day, the exact dose depending on the age, weight and condition of the patient or animal.

(c) Blood Pressure Lowering.

The novel prostacyclin analogs herein are useful as hypotensive agents to reduce blood pressure in mammals, including man. For this purpose, the compounds are administered by intravenous infusion at the rate about 0.01 to about 50 μg. per kg. of body weight per minute or in single or multiple doses of about 25 to 500 μg. per kg. of body weight total per day.

As for the antithrombic application described above, these compounds are most preferrable administered orally or by other convenient non-parenteral dosage form. In determining the appropriate oral dosage and frequency of administration titration of dose in conjunction other antihypertensive drugs being concomitantly administered is required. When used as the sole antihypertensive agent, determining the minimum effective dose required for adequate control of blood pressure is undertaken by initiating therapy at or near the threshold dose of patent or animal response. Thereafter upward adjustment of the dosage, until full control is achieved or undesired side effects are observed, is undertaken. Accordingly threshold dosages of 0.01 to 1.0 mg./kg. of body weight are employed.

(d) Gastric Secretion Reduction

The novel prostacyclin analogs herein are also useful in mammals, including man and certain useful animals, e.g., dogs and pigs, to reduce and control gastric secretion, thereby reduce or avoid gastrointestinal ulcer formation, and accelerate the healing of such ulcers already present in the gastrointestinal tract. For this purpose, these compounds are injected or infused intravenously, subcutaneously, or intramuscularly in an infusion dose range about 0.1 μg. to about 20 μg. per kg. of body weight per minute, or in a total daily dose by injection or infusion in the range about 0.01 to about 10 mg. per kg. of body weight per day, the exact dose depending on the age, weight, and condition of the patient or animal, and on the frequency and route of administration.

Preferably, however, the novel prostacyclin analogs are administered orally or by other nonparenteral routes. As employed orally, one to 6 administrations daily in a dosage range of about 1.0 to 100 mg./kg. of body weight per day is employed. Once healing of the ulcers has been accomplished the maintenance dosage required to prevent recurrence is adjusted downward so long as the patient or animal remains asymptomatic.

(e) NOSAC-Induced Lesion Inhibition.

The novel prostacyclin analogs herein are also useful in reducing the undesirable gastrointestinal effects resulting from systemic administration of antiinflammatory prostaglandin synthetase inhibitors, and are used for that purpose by concomitant administration of the prostaglandin derivative and the anti-inflammatory prostaglandin synthetase inhibitor. See Partridge et al., U.S. Pat. No. 3,781,429, for a disclosure that the ulcerogenic effect induced by certain non-steroidal anti-inflammatory agents in rats is inhibited by concomitant oral administration of certain prostaglandins. Accordingly the novel prostacyclin analogs herein are useful, for example, in reducing the undesirable gastrointestinal effects resulting from systemic administration of indomethacin, phenylbutazone, and aspirin. These are substances specifically mentioned in Partridge et al. as non-steroidal, anti-inflammatory agents. These are also known to be prostaglandin synthetase inhibitors.

The anti-inflammatory synthetase inhibitor, for example indomethacin, aspirin, or phenylbutazone is administered in any of the ways known in the art to alleviate an inflammatory condition, for example, in any dosage regimen and by any of the known routes of systemic administration.

The prostacyclin analog is administered along with the anti-inflammatory prostaglandin synthetase inhibitor either by the same route of administration or by a different route. For example, if the antiinflammatory substance is being administered orally, the novel prostacyclin analog is also administered orally, or, alternatively, is administered rectally in the form of a suppository or, in the case of women, vaginally in the form of a suppository or a vaginal device for slow release, for example as described in U.S. Pat. No. 3,545,439. Alternatively, if the antiinflammatory substance is being administered rectally, the novel prostacyclin analog is also administered rectally. Further, the novel prostacyclin analog can be conveniently administered orally or, in the case of women, vaginally. It is especially convenient when the administration route is to be the same for both anti-inflammatory substance and novel prostacyclin analog, to combine both into a single dosage form.

The dosage regimen for the novel prostacyclin analog in accord with this treatment will depend upon a variety of factors, including the type, age, weight, sex and medical condition of the mammal, the nature and dosage regimen of the antiinflammatory synthetase inhibitor being administered to the mammal, the sensitivity of the particular prostacyclin analog to be administered. For example, not every human in need of an antiinflammatory substance experiences the same adverse gastrointestinal effects when taking the substance. The gastrointestinal effects will frequently vary substantially in kind and degree. But it is within the skill of the attending physician or veterinarian to determine that administration of the antiinflammatory substance is causing undesirable gastrointestinal effects in the human or animal subject and to prescribe an effective amount of the novel prostacyclin analog to reduce and then substantially to eliminate those undesirable effects.

(f) Bronchodilitation.

The novel prostacyclin analogs herein are also useful in the treatment of asthma. For example, these compounds are useful as bronchodilators or as inhibitors of mediators, such as SRS-A, and histamine which are released from cells activated by an antigen-antibody complex. Thus, these compounds control spasm and facilitate breathing in conditions such as bronchial bronchitis, bronchiectasis, pneumonia and emphysema. For these purposes, these compounds are administered in a variety of dosage forms, e.g., orally in the form of tablets, capsules, or liquids; rectally in the form of suppositories; parenterally, subcutaneously, or intramuscularly, with intravenous administration being preferred in emergency situations; by inhalation in the form of aerosols or solutions for nebulizers; or by insufflation in the form of powder. Doses in the range of about 0.01 to 5 mg. per kg. of body weight are used 1 to 4 times a day, the exact dose depending on the age, weight, and condition of the patient and on the frequency and route of administration. For the above use these prostacyclin analogs can be combined advantageously with other anti-asthmatic agents, such as sympathomimetics (isoproterenol, phenylephrine, ephedrine, etc.); xanthine derivatives (theophylline and aminophylline); and corticosteroids (ACTH and prednisolone).

These compounds are effectively administered to human asthma patients by oral inhalation or by aerosol inhalation. For administration by the oral inhalation route with conventional nebulizers or by oxygen aerosolization it is convenient to provide the instant active ingredient in dilute solution, preferably at concentrations of about 1 part of medicament to form about 100 to 200 parts by weight of total solution. Entirely conventional additives may be employed to stabilize these solutions or to provide isotonic media, for example, sodium chloride, sodium citrate, citric acid, sodium bisulfite, and the like can be employed. For administration as a self-propelled dosage unit for administering the active ingredient in aerosol form suitable for inhalation therapy the composition can comprise the active ingredient suspended in an inert propellant (such as a mixture of dichlorodifluoromethane and dichlorotetrafluoroethane) together with a co-solvent, such as ethanol, flavoring materials and stabilizers. Instead of a co-solvent there can also be used a dispensing agent such as oleyl alcohol. Suitable means to employ the aerosol inhalation therapy technique are described fully in U.S. Pat. No. 2,868,691 for example.

(g) Nasal Decongestion.

The novel prostacyclin analogs herein are useful in mammals, including man, as nasal decongestants and are used for this purpose in a dose range of about 10 $\mu$g. to about 10 mg. per ml. of a pharmacologically suitable liquid vehicle or as an aerosol spray, both for topical application.

(h) Peripheral Vascular Circulatory Improvement.

These compounds are also useful in treating peripheral vascular disease in humans. The term peripheral vascular disease as used herein means disease of any of the blood vessels outside of the heart and disease of the lymph vessels, for example, frostbite, ischemic cerebrovascular disease, artheriovenous fistulas, ischemic leg ulcers, phlebitis, venous insufficiency, gangrene, hepatorenal syndrome, ductus arteriosus, non-osbtructuve mesenteric ischemia, arteritis lymphangitis and the like. These examples are included to be illustrative and should not be construed as limiting the term peripheral vascular disease. For these conditions the compounds of this invention are administered orally or parenterally via injection or infusion directly into a vein or artery, intravenous or intraarterial injections being preferred. The dosages of these compounds are in the range of 0.01-1.0 $\mu$g./kg. of body weight administered by infusions at an hourly rate or by injection on a daily basis, i.e. 1-4 times a day, the exact dose depending on the age, weight, and condition of the patient and on the frequency and route of administration. Corresponding oral doses are in the range 0.05-50 mg. every 2 hrs. during up to a maximum of 6 administrations daily. Treatment is continued for one to five days, although three days is ordinarily sufficient to assure long-lasting therapeutic action. In the event that systemic or side effects are observed the dosage is lowered below the threshold at which such systemic or side effects are observed.

(i) Reproduction and Fertility Control.

The novel prostacyclin analogs herein are useful in place of oxytocin to induce labor in pregnant female animals, including man, cows, sheep, and pigs, at or near term, or in pregnant animals with intrauterine death of the fetus from about 20 weeks to term. For this purpose, the compound is infused intravenously at a dose of 0.01 to 50 μg. per kg. of body weight per minute until or near the termination of the second stage of labor, i.e., expulsion of the fetus. These compounds are especially useful when the female is one or more weeks post-mature and natural labor has not started, or 12 to 60 hours after the membranes have ruptured and natural labor has not yet started. An alternative route of administration is oral, or other parenteral routes (e.g., intramuscular).

These compounds are further useful for controlling the reproductive cycle in menstruating female mammals, including humans. By the term menstruating female mammals is meant animals which are mature enough to menstruate, but not so old that regular menstruation has ceased. For that purpose the compound is administered systemically at a dose level in the range 0.01 mg. to about 20 mg. per kg. of body weight of the female mammal, advantageously during a span of time starting approximately at the time of ovulation and ending approximately at the time of menses or just prior to menses. Intravaginal and intrauterine routes are alternate methods of administration. Additionally, expulsion of an embryo or a fetus is accomplished by similar administration of the compound during the first or second trimester of the normal mammalian gestation period.

These compounds are further useful in causing cervical dilation in pregnant and nonpregnant female mammals for purposes of gynecology and obstetrics. In labor induction and in clinical abortion produced by these compounds, cervical dilation is also observed. In cases of infertility, cervical dilation produced by these compounds is useful in assisting sperm movement to the uterus. Cervical dilation by these compounds is also useful in operative gynecology such as D and C (Cervical Dilation and Uterine Curettage) where mechanical dilation may cause performation of the uterus, cervical tears, or infections. It is also useful for diagnostic procedures where dilation is necessary for tissue examination. For these purposes, these compounds are administered locally or systemically.

These compounds, for example, are administered orally or vaginally at doses of about 5 to 50 mg. per treatment of an adult female human, with from one to five treatments per 24 hour period. Alternatively these compounds are administered intramuscularly or subcutaneously at doses of about one to 25 mg. per treatment. The exact dosages for these purposes depend on the age, weight, and condition of the patient or animal.

These compounds are further useful in domestic animals (1) as an abortifacient (especially for feedlot heifers), (2) as an aid to estrus detection, and (3) as regulators of the estrus. Domestic animals include horses, cattle, sheep, and swine. The regulation or synchronization of estrus allows for more efficient management of both conception and labor by enabling a herdsman to breed all female animals in short, pre-defined intervals. This synchronization results in a higher percentage of live births than the percentage achieved by natural control and, moreover, is especially important in facilitating artificial insemination (AI), by permitting a more economic insemination operation. These compounds are injected or applied in a feed at doses of 0.1–100 mg. per animal and may be combined with other agents such as steroids. Dosing schedules will depend on the species treated. For example, mares are given these compounds 5 to 8 days after ovulation and return to estrus. Cattle are likewise treated after ovulation, but may thereafter require an additional administration to advantageously bring all into estrus at the same time.

(j) Renal Blood Flow Alteration.

The novel prostacyclin analogs herein increase the flow of blood in the mammalian kidney, thereby increasing volume and electrolyte content of the urine. For that reason, these compounds are useful in managing cases of renal dysfunction, especially those involving blockage of the renal vascular bed. Illustratively, these compounds are useful to alleviate and correct cases of edema resulting, for example, from massive surface burns, and in the management of shock. For these purposes, these compounds are preferably first administered by intravenous injection at a dose in the range 10 to 1000 μg. per kg. of body weight or by intravenous infusion at a dose in the range 0.1 to 20 μg. per kg. of body weight per minute until the desired effect is obtained. Subsequent doses are given by intravenous, intramuscular, or subcutaneous injecton or infusion in the range 0.05 to 2 mg. per kg. of body weight per day.

(k) Dermatosis Reversal.

The novel prostacyclin analogs herein are useful for treating proliferating skin diseases of man and domesticated animals, including psoriasis, atopic dermatitis, non-specific dermatitis, primary irritant contact dermatitis, allergic contact dermatitis, basal and squamous cell carcinomas of the skin, lamellar ichthyosis, epidermolytic hyperkeratosis, premalignant sun-induced keratosis, non-malignant keratosis, acne, and seborrheic dermatitis in humans and atopic dermatitis and mange in domesticated animals. These compounds alleviate the symptoms of these proliferative skin diseases: psoriasis, for example, being alleviated when a scale-free psoriasis lesion is noticeably decreased in thickness or noticeably, but incompletely cleared, or completely cleared.

For these purposes, these compounds are applied topically as compositions including a suitable pharmaceutical carrier, for example as an ointment, lotion, paste, jelly, spray, or aerosol, using topical bases such as petrolatum, lanolin, polyethylene glycols, and alcohols. These compounds, as the active ingredients; constitute from about 0.1% to about 15% by weight of the composition, preferably from about 0.5% to about 2%. In addition to topical administration, injection may be employed, as intradermally, intra- or peri-lesionally, or subcutaneously, using appropriate sterial saline compositions.

(l) Inflammation Reduction.

The novel prostacyclin analogs herein are useful as antiinflammatory agents for inhibiting chronic inflammation in mammals including the swelling and other unpleasant effects thereof using methods of treatment and dosages generally described for the therapeutic agents in U.S. Pat. No. 3,885,041, which patent is incorporated herein by reference.

(m) Reduction of Intraocular Pressure

The novel prostacyclin analogs herein are finally useful in man for the reduction of intraocular pressure in those disease states where abnormally elevated pressure in the eye is a threat to the sight of the patient (i.e., glaucoma). While many routes of administration are successfully employed for this purpose, direct application of a sterile ophthalmic solution (e.g., in the form of drops) is the preferred route for convenience and minimization of systemic effects. While ultimate dosage is readily determined by patient response in the exhibition of significantly lower intraocular pressure and the absence of localized side effects, such as irritation of eye tissues, initial dosage levels of about 0.05 mg. to 50 mg. per several drops of sterile ophthalmic solution, repeated 2 to 4 times per day, are employed.

The novel prostacyclin analogs herein are thus surprisingly and unexpectedly useful for a wide variety of pharmacological purposes, rendering these compounds pharmacological as well as structural analogs of prostacyclin. Moreover, the prostacyclin analogs herein exhibit a more prolonged chemical stability, facilitating their formulation and use as pharmacological agents. Finally, these novel prostacyclin analogs exhibit improved utility as compared to prostacyclin when employed, as described above, as antithrombotic, antiasthma, or antiinflammatory agents. This improved utility is evidenced in that the novel prostacyclin analogs of this invention exhibit increased potency or selectivity of action, thus exhibiting fewer undesirable side effects when administered for one of these preferred pharmacological uses.

Within the scope of the novel prostacyclin analogs described above, certain compounds are preferred in that they exhibit increased potency, selectivity of action, or otherwise represent especially convenient and useful agents, especially for the preferred uses described above.

Accordingly, preferred compounds are those wherein p and q are the integer 0 and r is one. Further, those compounds are preferred wherein $R_2$ is hydrogen. With respect to $Z_1$, preferred compounds are those wherein $Z_1$ is $-(CH_2)_g-CH_2-CH_2-$. Further, g is preferably the integer zero or 2, most preferably being zero. With respect to the $Y_1$ moiety, preferred compounds are those wherein $Y_1$ is trans—$CH=CH$—, —$CH_2CH_2$— or —$C\equiv C$—, the most especially preferred compounds being those wherein $Y_1$ is trans—$CH=CH$—. With respect to the $M_1$ moiety, preferred compounds are those wherein $M_1$ is

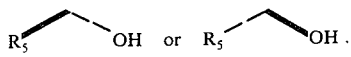

$R_5$ is preferably hydrogen, methyl, or ethyl, most preferably being hydrogen or methyl.

With respect to the $L_1$ moiety, those compounds wherein $R_3$ and $R_4$ are the same are preferred. Further preferred are those compounds herein wherein at least $R_3$, $R_4$, and $R_5$ is hydrogen. In the event $Y_1$ is cis—$CH=CH$— or —$C\equiv C$—, compounds wherein $R_3$, $R_4$, and $R_5$ are all hydrogen are preferred.

With respect to the integers m, h, and s, it is preferred that m be the integer 3, h be the integer zero or one and s be the integer 0 or one. Further, T is preferably chloro, fluoro, or trifluoromethyl.

Further preferred are the carboxylic acids or derivatives, i.e., esters, especially the p-substituted phenyl esters, and amides. For the above compounds which are amino or imino acids, the Zwitterions are a convenient form for isolation. With respect to the novel amides herein, preferred compounds are those wherein $R_{21}$ and $R_{22}$ are preferably hydrogen or alkyl of 1 to 8 carbon atoms, inclusive, being the same or different, preferably with the total number of carbon atoms in $R_{21}$ and $R_{22}$ being less than or equal to 8. More especially preferred are those amides wherein $R_{21}$ and $R_{22}$ are hydrogen or alkyl of one to 4 carbon atoms, inclusive, being the same or different, with the total number of carbon atoms in $R_{21}$ and $R_{22}$ being less than or equal to 4. Further, $R_{23}$ is preferably hydrogen.

The charts herein describe the method by which the novel prostacyclin analogs herein are prepared from known or readily synthesized starting materials.

With respect to these charts, q, r, $Z_1$, $X_1$, $L_1$, $R_7$, $M_1$, $R_2$, $Z_4$, and $Z_2$ are as defined above.

$R_{12}$ is $-OR_{10}$, $CH_2OR_{10}$, or hydrogen, wherein $R_{10}$ is a readily acid hydrolyzable blocking group such as tetrahydrofuranyl or tetrahydropyranyl. For examples of blocking groups especially contemplated by the present invention see U.S. Pat. No. 4,016,184, issued Apr. 5, 1977.

Further, $X_2$ is $-COOR_{11}$, $-CH_2R_{10}$, or $-COL_4$, wherein $R_{11}$ is an ester within the scope of $R_1$, wherein $R_1$ is defined above and $R_{10}$ and $L_4$ are as defined above.

$M_6$ is

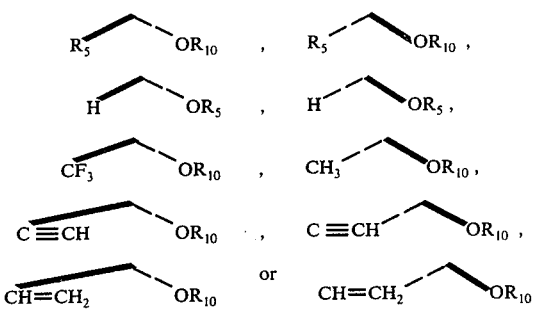

wherein $R_5$ and $R_{10}$ are as defined above. $R_{13}$ is alkyl or arylylsulfonyl, particularly being p-toluenesulfonyl.

$X_3$ is $-COOR_{11}$, $-CH_2OH$, $-COL_4$, wherein $R_{11}$ and $L_4$ are as defined above.

CHART A

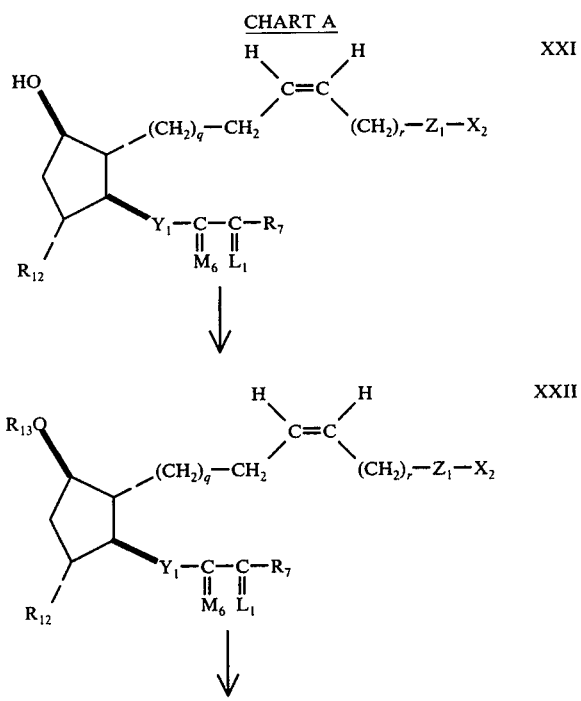

-continued
CHART A
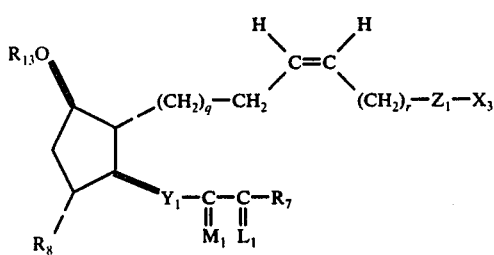
XXIII
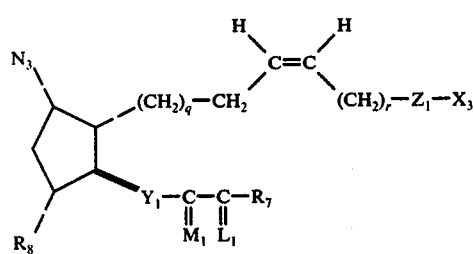
XXIV
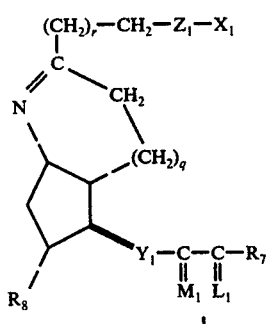
XXV
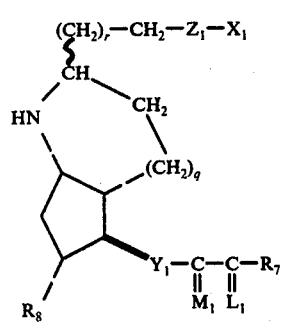
XXVI
-continued
CHART A
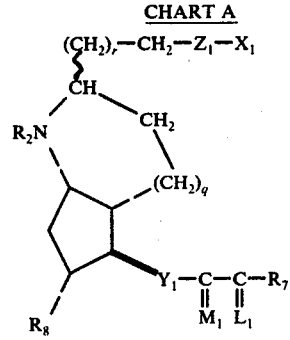
XXVII
CHART B
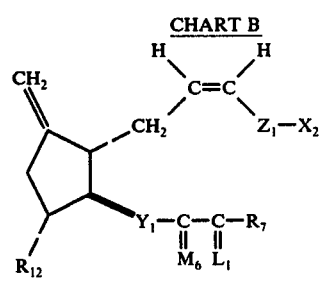
XXX
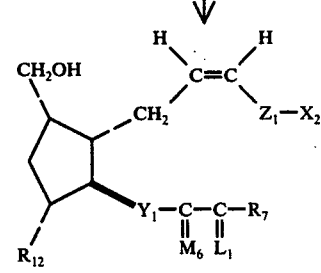
XXXI
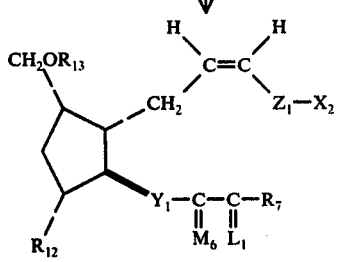
XXXII
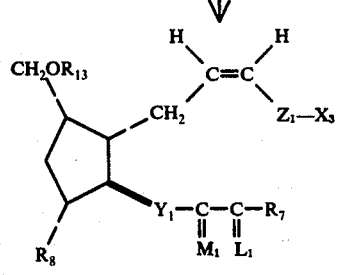
XXXIII -continued
CHART B

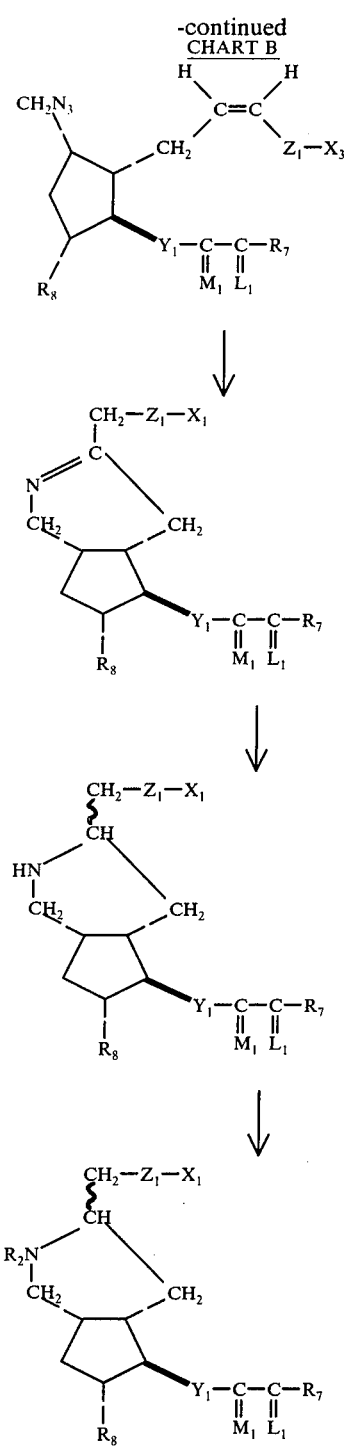

XXXIV

XXXV

XXXVI

XXXVII

With respect to Chart A a method is provided whereby the formula XXI PGF$_2\beta$ or cis-4,5-didehydro-PGF$_1\beta$ compound is transformed to the novel prostacyclin analogs of formula XXV-XXVII.

The various formula XXI compounds employed as starting materials in the present synthesis are conveniently prepared from known or readily available starting materials. For example, methods are known in the art for the transformation of corresponding PGF$_2\alpha$ or cis-4,5-PGF$_1\alpha$ type compounds to corresponding PGF$_2\beta$ or cis-4,5-didehydro PGF$_1\beta$ compounds. Further, PGE$_2$ or cis-4,5-didehydro-PGE$_1$ type compounds are likewise reduced to the corresponding PGF$_2\beta$ or cis-4,5-didehydro PGF$_1\beta$ type compounds. Further, formula XXI encompasses compounds deoxygenated at C-11 (11-deoxy-PG-type compounds) or substituted at C-11 by an hydroxymethyl in place of the hydroxy (11-deoxy-11-hydroxymethyl-PG-type compounds). These compounds are prepared by methods known in the art from corresponding PGA$_2$ or cis-4,5-didehydro PGA$_1$ type compounds. Such PGA$_2$ or cis-4,5-didehydro PGA$_1$ type compounds are conveniently prepared by acid dehydration of the corresponding PGE$_2$ or cis-4,5-didehydro-PGE$_1$ type compounds referred to above. Thus, all of the various compounds within the scope of formula XXI represent either known prostaglandin analogs or can be readily prepared by employment of conventional chemical reactions on known prostaglandin type starting materials.

As is further apparent from inspection of formula XXI, the PGF$_2\beta$ or cis-4,5-didehydro-PGF$_1\beta$ compounds depicted therein are in mono-, bis-, or tris-etherated form, whereby the respective hydroxyls, except for the C-9 hydroxy are transformed to corresponding ether derivatives. Ether groups are selected from those blocking groups known to be successfully and conventionally employed in this synthesis of prostaglandin type products from various intermediates, being readily hydrolyzable under acid conditions. Most particularly, tetrahydrofuranyl is a convenient and readily available moiety employed for such purposes.

The formula XXII is thereafter prepared from the formula XXI compound by transformation of the C-9 hydroxyl to its alkyl- or arylylsulfonyl derivative. Such alkyl- or arylylsulfonates are prepared by conventional methods. For example, the acid chloride corresponding to the alkyl- or arylylsulfonyl derivative to be prepared is reacted with the formula XXI compound in the presence of a tertiary amine base. Accordingly, by a preferred method for this transformation, p-toluenesulfonyl chloride in the presence of pyridine is reacted with the formula XXI compound to produce the corresponding formula XXII formula p-toluenesulfonyl derivative. While numerous conventional organic solvents are employed in this reaction, in appropriate cases, the amine base may be employed as the reaction solvent. While the reaction proceeds over a wide range of temperatures, for convenience ambient temperatures are preferred.

The formula XXII compound is thereafter transferred to the formula XXIII compound by hydrolysis of the blocking groups according to R$_{10}$. The hydrolysis of thses blocking groups proceeds under mild acidic conditions, as is known for the hydrolysis of such blocking groups when employed with prostaglandins and prostaglandin analogs. For example, a mixture of acetic acid, tetrahydrofuran, and water (3:1:1, by volume) is a conventional method by which such hydrolysis is accomplished.

Thereafter, the formula XXIII compound is further converted to the formula XXI azide by reaction with sodium azide in the presence of hexamethylphosphoramide. For this purpose, the prostaglandin is conveniently dissolved in hexamethylphosphoramide and thereafter solid sodium azide is added with stirring under a nitrogen atmosphere. In order to maintain a reasonable reaction rate, the reaction mixture is initially run at 30° to 50° C. for several hours and thereafter cooled to 0° to −20° C. whereupon pure formula XXII product is recovered by conventional methods of base extraction and purification.

Further, the formula XXI compound is obtained from the formula XXIV by cyclization. This cyclization is obtained by first dissolving the formula XXIV product in a suitable organic solvent (e.g., ethyl acetate) and thereafter heating the reaction mixture to high temperature (e.g., 60°–90° C.) until thin layer chromatographic analysis indicates the reaction mixture to be complete. While at lower reaction temperatures several days may be required for completion of the reaction, at temperatures of about 80° C. the reaction is ordinarily complete within 24 hours. In those cases where formula XXIV esters are hydrolyzed during or following the cyclization, esterification of the cyclized product is accomplished by conventional techniques, thus yielding the formula XXV product.

Following preparation of the formula XXV prostacyclin analogs, the formula XXVI prostacyclin analogs are prepared therefrom by borohydride reduction. For example, sodium borohydride is employed at moderate temperature (0°–30° C.). The 6α and 6β isomers (when q is zero) or 5α and 5β isomers (when q is one) are obtained by conventional means of separation of diastereomeric mixtures (e.g., chromatography). In most instances the 6β isomer is readily distinguished from the 6α isomer, being the more polar isomer in most solvent systems by TLC (thin layer chromatography).

Further, the formula XXVI compound is thereafter transformed to the corresponding formula XXVII compound by acylation or alkylation, depending upon whether $R_2$ is alkyl or acyl, respectively. For the alkylation, the corresponding alkyl iodide will produce the desired formula XXVII alkylated product. For the acylated product, the acid anhydride or acid chloride is reacted with the formula XXVI product in the presence of a tertiary amine base followed by saponification of any esters (e.g., in methanolic sodium bicarbonate).

Chart B provides a method whereby the synthesis of novel prostacyclin analogs according to formula I wherein p is one are prepared. By the method described in Chart B, the formula XXX 9-deoxy-9-methylene-PGF-type compound is first prepared by known methods. For example, this 9-deoxy-9-methylene-PGF-type compound is prepared from the corresponding PGE-type compound by the method described in U.S. Pat. No. 3,950,363, particularly the transformation of the formula XX compound to the formula XXI compound at column 9–12 therein.

After the preparation of this 9-deoxy-9-methylene-PGF-type compound, the corresponding 9-deoxy-9-hydroxymethyl-PGF-type compound is prepared by known methods. For example, see the disclosure in U.S. Pat. No. 3,950,363, where the formula XXI compound therein (9-deoxy-9-methylene-PGF-type compound referred to above) is subjected to hydroboration and oxidation, thereby yielding the desired formula XXXI product herein. Thereafter this formula XXXI product of Chart B is transformed to the various formula XXXII–XXXIX compounds by the methods described in Chart A for the transformation of the formula XXI compound to the formula XXII–XXIX compounds respectively.

According to the above charts, the novel prostacyclin analogs herein are obtained first as primary alcohols, esters, or amides. When, however, the corresponding carboxylic acids are desired, these acids are prepared by hydrolysis of the corresponding ester using conventional methods. For example, the hydrolysis proceeds by reacting the esterified form of the prostacyclin analog with base in a water-alkanol mixture. Thus, sodium hydroxide and methanol is employed to hydrolyze the ester to the corresponding sodium salt.

In order to recover the resultant amino and imino acid, conventional isolation techniques for recovering such compounds are employed. For example, recovery of the amino or imino acid proceeds by first removing the organic solvent (e.g., methanol) under reduced pressure, neutralizing the resulting mixture (e.g., with hydrochloric acid), and subjecting this mixture to a resin capable of binding amino or imino acids. Particularly useful resins for this purpose are neutral resins (i.e, those exhibiting neither acidic or basic functionalities).

With the crude imino or amino acid on the resin, successive elution with water (for removal of salts) and an organic solvent (e.g., an alkanol such as methanol) yields a solvated mixture containing the amino or imino acid, which is then recovered in pure form by evaporation of solvent and lyophilizing the residue.

The pharmacologically acceptable salts of these carboxylic acids are then obtained by neutralization with a corresponding base. Conventional techniques of isolation and recovery of the salt are employed.

When the acid addition salts are desired, reaction of the prostacyclin analog with the acid corresponding to the acid addition salt to be prepared yields the desired product.

An alternative method for the preparation and recovery of carboxy-containing prostacyclin analogs is by hydrolysis of the formula XXIV or formula XXXIV ester prior to the cyclization step, yielding the formula XXV and XXXV products, respectively. In this case, the prostacyclin analog in the free acid form is obtained directly from the resulting reaction mixture by conventional means.

DESCRIPTON OF THE PREFERRED EMBODIMENTS

The invention can be more fully understood by the following examples and preparations.

All temperatures are in degrees centigrade.

IR (infrared) absorption spectra are recorded on a Perkin-Elmer Model 421 infrared spectrophotometer. Except when specified otherwise, undiluted (neat) samples are used.

UV (Ultraviolet) spectra are recorded on a Cary Model 15 spectrophotometer.

NMR (Nuclear Magnetic Resonance) spectra are recorded on a Varian A-60, A-60D, or T-60 spectrophotometer in deuterochloroform solutions with tetramethylsilane as an internal standard (downfield).

Mass spectra are recorded on an CEG model 110B Double Focusing High Resolution Mass Spectrometer on an LKB Model 9000 Gas-Chromatograph-Mass Spectrometer. Trimethylsilyl derivatives are used, except where otherwise indicated.

"Brine", herein, refers to an aqueous saturated sodium chloride solution.

The A-IX solvent system used in thin layer chromatography is made up from ethyl acetate-acetic acid-2,2,4-trimethylpentane-water (90:20:50:100) according to M. Hamberg and B. Samuelsson, J. Biol. Chem. 241, 257 (1966).

Skellysolve-B (SSB) refers to mixed isomeric hexanes.

Silica gel chromatograpy, as used herein, is understood to include elution, collection of fractions, and combination of those fractions shown by TLC (thin layer chromatography) to contain the pure produce (i.e., free of starting material and impurities).

Melting points (MP) are determined on a Fisher-Johns or Thomas-Hoover melting point apparatus.

THF refers to tetrahydrofuran.

Specific Rotations, [α], are determined for solutions of a compound in the specified solvent at ambient temperature with a Perkin-Elmer Model 141 Automatic Polarimeter.

EXAMPLE 1

9-deoxy-9α,6-nitrilo-PGF$_1$ (Formula III: $p$ and $q$ are zero and r is one, $Z_2$ is

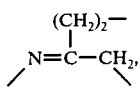

$Z_1$ is —(CH$_2$)$_3$—, $X_1$ is —COOH, $R_8$ is hydroxy, $Y_1$ is trans—CH═CH—, $M_1$ is

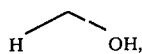

$R_3$ and $R_4$ of the $L_1$ moiety are both hydrogen, and $R_7$ is n-butyl)

Refer to Chart A.

A. To a mixture of 9.1 gms of PGF$_{2\beta}$, methyl ester, 11,151 -bis(tetrahydropyranyl ether) and 100 ml of dry pyridine is added 3.87 gms of p-toluenesulfonyl chloride. Resulting mixture is stirred at ambient temperature for 12 hrs and thereafter an additional 1.19 gms of p-toluenesulfonyl chloride is added. After stirring an additional 12 hrs, the resulting mixture is cooled in an ice bath and 20 ml of water is added with stirring over 15 min. The resulting mixture is then poured into a mixture of ice brine and extracted with diethyl ether. The ethereal extracts are then washed with aqueous sodium bicarbonate, brine, and dried over sodium sulfate. Accordingly, there is obtained 11.1 gms of PGF$_{2\beta}$, methyl ester, 11,15-bis(tetrahydropyranyl ether), 9-(p-toluenesulfonate).

B. The reaction product of part A is dissolved in a mixture of tetrahydrofuran, water, and acetic acid (40 ml, 40 ml, and 120 ml, respectively), and the reaction mixture warmed to 40° C. for 3.5 hours under a nitrogen atmosphere.

After cooling to ambient temperature, the resulting mixture is then washed with brine and extracted with a mixture of ethyl acetate and hexane (1:1). Successive washings with brine, sodium bicarbonate and brine yield an organic phase which is then washed with sodium sulfate and concentrated under reduced pressure to yield 8.3 gms of crude PGF$_{2\beta}$, methyl ester, 9-(p-toluenesulfonate). This crude product is then chromatographed on 1.3 kg of neutral silica gel, eluting with 50-70% ethyl acetate in hexane and yielding 4.475 gms of pure product.

C. The reaction product of part B is then dissolved in 100 ml of hexamethylphosphoramide and thereafter under a nitrogen atmosphere there is added 10 gm of solid sodium azide. The resulting mixture is then stirred for 2 hrs at 40° C. and thereafter cooled to −10° C. Into the cooled mixture is added 600 ml of ice water and thereafter diethyl ether extracts are obtained. These ethereal extracts are then washed with water and brine, dried over magnesium sulfate, and concentrated under reduced pressure, yielding a crude formula XXIV product.

D. The crude product of part C dissolved in 10 ml of methanol is then cooled to about 0° C. in an ice bath. Thereafter 10 ml of 3N aqueous potassium hydroxide is added dropwise. After removal from the ice bath, the resulting mixture is stirred at ambient temperature for 2.5 hours and thereafter poured into a mixture of brine ice and 2N aqueous potassium bisulfate. Extraction with ethyl acetate and washing of the organic extracts with brine is then followed by drying and evaporating under reduced pressure, yielding pure free acid corresponding to the methyl ester of part C.

E. The reaction product of part D in 100 ml of ethyl acetate is heated to 60° C. for 1 hr to 70° C. for 1 hr, and thereafter to 80° C. for 14 hrs under a nitrogen atmosphere. Thereafter, crude title product is obtained by evaporation of the ethyl acetate solvent and chromatographing the residue on 120 gms of acid washed silica gel. Eluting with 30% methanol and ethyl acetate yields 736 mg of pure title product. Infrared absorption are observed at 3250, 2600, 2500, 1900, 1700, 1630, 1550, 1080, 960, and 120 cm$^{-1}$. NMR absorptions are observed at 5.6–5.45, 4.65–3.5, and 0.9 δ.

EXAMPLE 2

9-deoxy-9α,6-nitrilo-PGF$_1$, methyl ester.

Refer to Chart A.

A. The crude methyl ester of Example 1, part C, is chromatographed on 15 gm of neutral silica gel eluting with 80% ethyl acetate in hexane yielding pure 9-deoxy-9α-azido-PGF$_2$, methyl ester. Infrared absorptions are observed at 3360, 2100, 1735, 1670, 1325, 1260, 1165, 1080, 965 cm$^{-1}$. NMR absorptions are observed at 5.7–5.1, 4.2–3.5, 3.66, and 2.8 δ, A solution of 160 mg of the reaction product of part A and 5 ml of ethyl acetate is allowed to stand for 2 hrs at 50° C. under a nitrogen atmosphere. Thereafter, the mixture is heated to 60° C. for 2 hrs and finally to 80° C. for 2 additional hrs. After completion of heating, the reaction mixture is cooled to 10° C. and concentrated under reduced pressure. A residue (137 mg) is then chromatographed on 15 gms of silica gel. Eluting with 20% methanol and ethyl acetate yields pure title product (100 mg) as a crystalline product. Recrystallization from ethyl acetate and hexane yields 60 mg of pure material with melting point 52°–54° C. Infrared absorptions are observed at 3350, 1735, 1640, 1455, 1435, 1300, 1235, 1195, 1170, 1135, 1090, 1025, and 970 cm$^{-1}$. NMR absorptions are observed at 5.62–5.4, 4.5–3.7, 3.67, and 3.55 δ. The mass spectrum exhibits a molecular ion at 365 and other peaks at 348, 336, 334, 294, and 265.

Following the procedures of Examples 1 and 2, but employing the various other PGFβ starting materials of formula XXI, there are prepared in free acid, amide, and methyl ester form each of the various corresponding formula XXV products.

EXAMPLE 3

(6R)- and 6S)-deoxy-6,9α-imino-PGF$_1$, methyl ester (Formula III: $q$ and $p$ are zero, $Z_2$ is

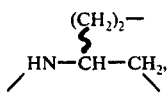

$Z_1$ is —$(CH_2)_3$, $X_1$ is $COOH_3$, $R_8$ is hydroxy, $Y_1$ is trans-$CH_1CH$—, $M_1$ is

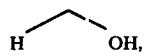

Rhd 3 and $R_{4\ 1\ of\ the\ L1}$ moiety are both hydrogen, and $R_7$ is n-butyl).
Refer to Chart A.

A solution of 2.5 g of the title product of Example 2 in 60 ml of dry methanol is stirred at ambient temperature and treated thereafter with 500 mg of sodium borohydride. After 1 hr of continued stirring at ambient temperature, a mixture of (6RS) products is obtained. This mixture is then poured into ice and brine, extracted with ethyl acetate, and the ethyl acetate extracts washed with brine, dried over sodium sulfate and concentrated under reduced pressure. Crude product (2.4 g) is then chromatographed on silica gel eluting with a mixture of methanol, chloroform, and triethylamine (10:90:2). Accordingly there are obtained 1.15 g of the (6R) isomer. Trituration with ethyl acetate yields 815 mg of a crystalline 6R title product. Melting point is 114°–115° C. Further there are obtained 1.33 g of the (6S)-isomer, being the more polar of the two isomers by TLC, which upon trituration with ethyl acetate yields 1.07 g of pure product. The melting point is observed at 116°–117° C.

For the 6R isomer, NMR absorptions are observed at 5.67–5.46, 5.33, 4.25–3.8, and 3.66 δ. For the 6S isomer, NMR absorptions are observed at 7.15, 5.76–5.50, 4.34–3,90, and 3.66 δ.

Following the procedure of Example 3, but employing each of the various 9-deoxy-9,6α-nitrilo-PGF-type compounds described following Example 2 place of 9-deoxy-9,6α-nitrilo-PGF$_2$ as employed in Example 3, there are obtained each of the various (6R) or (6S) -9-deoxy-6,9α-imino-PGF$_1$- type compounds of formula XXVI.

EXAMPLE 4

(6R)-9-deoxy-6,9α-amino-PGF$_1$

The title product of Example 3 (500 mg) in 3 ml of methanol is added to 3 ml of 1 N potassium hydroxide under a nitrogen atmosphere and stirred for 18 hrs at ambient temperature. Thereafter the nethanol is removed under reduced pressure and the resulting product eluted with water (2 ml) and acidified to pH 6.6 with dilute aqueous hydrochloric acid.

The resulting mixture is then lyophilized and the residue taken up in 3 ml of water and chromatographed on a 50 ml column of a neutral (i.e., non-basic and non-acidic) resin. Elution with water and methanol yields the title product in the methanolic fractions. This product is then concentrated under reduced pressure and the residue dissolved in 15 ml of water and lyophilized yielding 350 mg of a white hydroscopic aolid.

The hydroscopic solid (310 mg) in 50 ml of diethyl ether is then allowed to stand at ambient temperature for 60 hrs. Thereafter the product is filtered, washed with fresh diethyl ether, and dried under a nitrogen atmosphere, yielding 300 mg of pure title product.

Following the procedure described above the (6S) isomer (500 mg) yields 320 mg of (6S)-9-deoxy-6,9α-amino-PGF$_1$ (320 mg).

For the (6S) isomer the melting point is 186°–189° C. The high resolution mass spectrum for the trimethylsilyl derivative exhibits a demethylated molecular ion at 554.3528. The specific optical rotation is +39° at 0.983 gm per 100 ml in water. The C:H:N ratio is 67.73:9.52:3.92. Infrared absorptions are observed at 3370, 2680, 2560, 2450, 1630, 1540, 1405, 1335, 1100, 1085, 1045, 1020, and 970 cm$^{-1}$.

The mass spectrum for the trimethylsilyl derivative exhibits a weak molecular ion at 569 and a high resolution demethylated molecular ion at 554.3534. The specific optical rotation is 38° C. at 0.8875 gm per 100 ml in water. The C:H:N ratio is 68.03:9.79:3.97. Infrared absorptions are observed at 3420, 3320, 2650, 2400, 2330, 2240, 1640, 1540, 1405, 1345, 1105, 1050, and 975 cm$^{-1}$.

EXAMPLE 5

9-deoxy-9α,6-nitrilo-PGF$_1$, hydrochloride

The title product of Example 1 (700 mg) in 20 ml of water is mixed with stirring with 20 ml of aqueous 0.1 N hydrochloric acid. The mixture is lyophilized and the residue treated with 50 ml of anhydrous tetrahydrofuran. On stirring, crystallization occurs and after 45 min of additional stirring at ambient temperature and an additional 45 min at 0° C., the crystals are filtered and dried, yielding title product (735 mg). The mass spectrum of the tris(trimethylsilyl) derivative exhibits a high resolution peak at 567.3560.

The specific optical rotation in aqueous ethanol is +7°. the carbon:hydrogen:nitrogen:chlorine analysis is 61.38:9.11:3.49:9.21 %. The melting point is 72°–76° C.

EXAMPLE 6

N-Methyl-(6R)-9-deoxy-6,9α-imino-PGF$_2$α, methyl ester (Formula III: $Z_2$ is

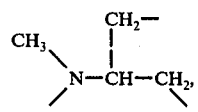

$Z_1$ is —$(CH_2)_3$—, $X_1$ is —$COOCH_3$, R is one and p and q are zero, $R_8$ is hydroxy, $Y_1$ is trans—CH=CH—, $M_1$ is

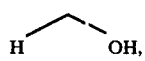

$R_3$ and $R_4$ are hydrogen and $R_7$ is N-butyl.
Refer to Chart A.

The title product of Example 3 is diluted in methanol and thereafter treated with a single stoichiometric equivalent of methyl iodide. The reaction mixture is then heated from ambient temperature to reflux for about 6 hrs.

As the reaction is shown to be complete, the reaction mixture is then cooled, made basic with dilute ammonium hydroxide (to pH 12). Title product is then obtained from the reaction mixture by extraction with ethyl acetate, washing the extracts, and concentrating the pure title product.

Following the procedure of Example 6, each of the various formula XXVI of formula XXXVI is transformed to corresponding formula XXVII or formula XXXVII compound wherein $R_2$ is methyl.

EXAMPLE 7

N-acetyl-(6R)-9-deoxy-6,9α-imino-PGF$_1$, methyl ester (Formula III: $Z_2$ is

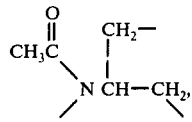

$Z_1$ is —(CH$_2$)$_3$—, $X_1$ is —COOCH$_3$, p and q are zero, $R_8$ is hydroxy, $Y_1$ is trans—CH=CH—, $M_1$ is

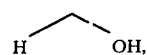

$R_3$ and $R_4$ are hydrogen, and $R_7$ is N-butyl.

The title product of Example 3 in pyridine is reacted with excess acetic anhydride at ambient temperature and thereafter with methanolic sodium bicarbonate at ambient temperature for several days. When chromatographic analysis indicates the deesterification to be complete, the title product is recovered by conventional separation and purification techniques.

Following the procedure of Example 7, but employing each of the various formula XXXVI or formula XXXVII compounds in place of the title compound of Example 3, there are obtained each of the various corresponding formula XXVII or formula XXXVII compounds wherein $R_2$ is acetyl.

Following the procedure of the above examples, but employing the appropriate PGF$_2$β-type, cis-4,5-didehydro-PFG$_2$β-type or 9-deoxy-9-hydroxymethyl-PGF$_2$β-type starting material, there are prepared
  9-deoxy-9α,6-nitrilo-PGF$_1$-type compounds;
  9-deoxy-9α,5-nitrilo-PGF$_1$-type compounds;
  9-deoxy-6,9α-nitrilomethylene-PGF$_1$-type compounds;
  6α- or 6β-9-deoxy-6,9α-imino-PGF$_1$-type compounds;
  5α- or 5β-9-deoxy-5,9α-imino-PGF$_1$-type compounds;
  6α- or 6β-9-deoxy-6,9α-iminomethylene-PGF$_1$-type compounds;
  6R- or 6S-N-methyl- or N-acetyl-9-deoxy-6,9α-imino-PGF$_1$ type compounds;
  5R- or 5S-N-alkyl- or N-acyl-9-deoxy-5,9α-imino-PGF$_1$-type compounds; or
  6R- or 6S-N-acetyl- or N-acetyl-9deoxy-6,9α-iminomethylene-PGF$_1$-type compounds
in free acid, amide, or ester form which exhibit the following side chain substituents:
  15-Methyl;
  16-Methyl;
  15,16-Dimethyl-;
  16,16-Dimethyl-;
  16-Fluoro-;
  15-Methyl-16-fluoro-;
  16,16-Difluoro-;
  15-Methyl-16,16-difluoro-;
  17-Phenyl-18,19,20-trinor-;
  17-(m-trifluoromethylphenyl)-18,19,20-trinor-;
  17-(m-chlorophenyl)-18,19,20-trinor-;
  17-(p-fluorophenyl)-18,19,20-trinor-;
  15-Methyl-17-phenyl-18,19,20-trinor-;
  16-Methyl-17-phenyl-18,19,20-trinor-;
  16,16-Dimethyl-17phenyl-18,19,20-trinor-;
  16-Fluoro-17-phenyl-18,19,20-trinor-;
  16,16-Difluoro-17-phenyl-18,19,20-trinor-;
  16-Phenyl-17,18,19,20-tetranor-;
  15-Methyl-16-phenyl-17,18,19,20-tetranor-;
  16-(m-trifluoromethylphenyl)-17,18,19,20-tetranor-;
  16-(m-chlorophenyl)-17,18,19,20-tetranor-;
  16-(p-fluorophenyl)-17,18,19,20-tetranor-;
  16-Phenyl-18,19,20-trinor-;
  15-Methyl-16-phenyl-18,19,20-trinor-;
  16-Methyl-16-phenyl-18,19,20-trinor-;
  15,16-Dimethyl-16-phenyl-18,19,20-trinor-;
  16-Phenoxy-17,18,19,20-tetranor-;
  15-Methyl-16-phenoxy-17,18,19,20-tetranor-;
  16-(m-trifluoromethylphenoxy)-17,18,19,20-tetranor-;
  16-(m-chlorophenoxy)-17,18,19,20-tetranor-;
  16-(p-fluorophenoxy)-17,18,19,20-tetranor-;
  16-Phenoxy-18,19,20-trinor-;
  15-Methyl-16-phenoxy-18,19,20-trinor-;
  16-Methyl-16-phenoxy-18,19,20-trinor-;
  15,16-Dimethyl-16-phenoxy-18,19,20-trinor-;
  13,14-Didehydro-;
  16-Methyl-13,14-didehydro-;
  16,16-Dimethyl-13,14-didehydro-;
  16-Fluoro-13,14-didehydro-;
  16,16-Difluoro-13,14-didehydro-;
  17-Phenyl-18,19,20-trinor-13,14-didehydro-;
  17-(m-trifluoromethylphenyl)-18,19,20-trinor-13,14-didehydro-;
  17-(m-chlorophenyl)-18,19,20-trinor-13,14-didehydro-;
  17-(p-fluorophenyl)-18,19,20-trinor-13,14-didehydro-;
  16-Methyl-17-phenyl-18,19,20-trinor-13,14-didehydro-;
  16,16-Dimethyl-17-phenyl-18,19,20-trinor-13,14-didehydro-;
  16-Fluoro-17-phenyl-18,19,20-trinor-13,14-didehydro-;
  16,16-Difluoro-17-phenyl-18,19,20-trinor-13,14-didehydro-;
  16-Phenyl-17,18,19,20-tetranor-13,14-didehydro-;
  16-(m-trifluoromethylphenyl)-17,18,19,20-tetranor-13,14-didehydro-;
  16-(m-chlorophenyl)-17,18,19,20-tetranor-13,14-didehydro-;
  16-Phenyl-18,19,20-trinor-13,14-didehydro-;
  16-Methyl-16-phenyl-18,19,20-trinor-13,14-didehydro-;
  16-Phenoxy-17,18,19,20-tetranor-13,14-didehydro-;
  16-(m-trifluoromethylphenoxy)-17,18,19,20-tetranor-13,14-didehydro-;
  16(m-chlorophenoxy)-17,18,19,20-tetranor-13,14-didehydro-;
  16-Phenoxy-18,19,20-trinor-13,14-didehydro-;
  16-Methyl-16-phenoxy-18,19,20-trinor-13,14-didehydro-;
  13,14-Dihydro-;
  16-Methyl-13,14-dihydro-;
  16,16-Dimethyl-13,14-dihydro-;
  16-Fluoro-13,14-dihydro-;
  16,16-Difluoro-13,14-dihydro-;
  17-Phenyl-18,19,20-trinor-13,14-dihydro-;

17-(m-trifluoromethylphenyl)-18,19,20-trinor-13,14-dihydro-;
17-(m-chlorophenyl)-18,19,20-trinor-13,14-dihydro-;
17-(p-fluorophenyl)-18,19,20-trinor-13,14-dihydro-;
16-Methyl-17-phenyl-18,19,20-trinor-13,14-dihydro-;
16,16-Dimethyl-17-phenyl-18,19,20-trinor-13,14-dihydro-;
16-Fluoro-17-phenyl-18,19,20-trinor-13,14-dihydro-;
16,16-Difluoro-17-phenyl-18,19,20-trinor-13,14-dihydro-;
16-Phenyl-17,18,19,20-tetranor-13,14-dihydro-;
16-(m-trifluoromethylphenyl)-17,18,19,20-tetranor-13,14-dihydro-;
16-(m-chlorophenyl)-17,18,19,20-tetranor-13,14-dihydro-;
16-(p-fluorophenyl)-17,18,19,20-tetranor-13,14-dihydro-;
16-Phenyl-18,19,20-trinor-13,14-dihydro-;
16-Methyl-16-phenyl-18,19,20-trinor-13,14-dihydro-;
16-Phenoxy-17,18,19,20-tetranor-13,14-dihydro-;
16-(m-trifluoromethylphenoxy)-17,18,19,20-tetranor-13,14-dihydro-;
16-(m-chlorophenoxy)-17,18,19,20-tetranor-13,14-dihydro-;
16-(p-fluorophenoxy)-17,18,19,20-tetranor-13,14-dihydro-;
16-Phenoxy-18,19,20-trinor-13,14-dihydro-;
16-Methyl-16-phenoxy-18,19,20-trinor-13,14-dihydro-;
13-cis-;
16-Methyl-13-cis-;
16,16-Dimethyl-13-cis-;
16-Fluoro-13-cis-;
16,16-Difluoro-13-cis-;
17-Phenyl-18,19,20-trinor-13-cis-;
17-(m-trifluoromethylphenyl)-18,19,20-trinor-13-cis-;
17-(m-chlorophenyl)-18,19,20-trinor-13-cis-;
17-(p-fluorophenyl)-18,19,20-trinor-13-cis-;
16-Methyl-17-phenyl-18,19,20-trinor-13-cis-;
16,16-Dimethyl-17-phenyl-18,19,20-trinor-13-cis-;
16-Fluoro-17-phenyl-18,19,20-trinor-13-cis-;
16,16-Difluoro-17-phenyl-18,19,20-trinor-13-cis-;
16-Phenyl-17,18,19,20-tetranor-13-cis-;
16-(m-trifluoromethylphenyl)-17,18,19,20-tetranor-13-cis-;
16-(m-chlorophenyl)-17,18,19,20-tetranor-13-cis-;
16-(p-fluorophenyl)-17,18,19,20-tetranor-13-cis-;
16-Phenyl-18,19,20-trinor-13-cis-;
16-Methyl-16-phenyl-18,19,20-trinor-13-cis-;
16-Phenoxy-17,18,19,20-tetranor-13-cis-;
16-(m-trifluoromethylphenoxy)-17,18,19,20-tetranor-13-cis-;
16-(m-chlorophenoxy)-17,18,19,20-tetranor-13-cis-;
16-(p-fluorophenoxy)-17,18,19,20-tetranor-13-cis-;
16-Phenoxy-18,19,20-trinor-13-cis-;
16-Methyl-16-phenoxy-18,19,20-trinor-13-cis-;
2,2-Difluoro-;
2,2-Difluoro-15-methyl-;
2,2-Difluoro-16-methyl-;
2,2-Difluoro-16,16-dimethyl-;
2,2-Difluoro-16-fluoro-;
2,2-Difluoro-16,16-difluoro-;
2,2-Difluoro-17-phenyl-18,19,20-trinor-;
2,2-Difluoro-17-(m-trifluoromethylphenyl)-18,19,20-trinor-;
2,2-Difluoro-17-(m-chlorophenyl)-18,19,20-trinor-;
2,2-Difluoro-17-(p-fluorophenyl)-18,19,20-trinor-;
2,2-Difluoro-16-methyl-17-phenyl-18,19,20-trinor-;
2,2-Difluoro-16,16-dimethyl-17-phenyl-18,19,20-trinor-;
2,2-Difluoro-16-fluoro-17-phenyl-18,19,20-trinor-;
2,2-Difluoro-16,16-difluoro-17-phenyl-18,19,20-trinor-;
2,2-Difluoro-16-phenyl-17,18,19,20-tetranor-;
2,2-Difluoro-16-(m-trifluoromethylphenyl)-17,18,19,20-tetranor-;
2,2-Difluoro-16-(m-chlorophenyl)-17,18,19,20-tetranor-;
2,2-Difluoro-16-(p-fluorophenyl)-17,18,19,20-tetranor-;
2,2-Difluoro-16-phenyl-18,19,20-trinor-;
2,2-Difluoro-16-methyl-16-phenyl-18,19,20-trinor-;
2,2-Difluoro-16-phenoxy-17,18,19,20-tetranor-;
2,2-Difluoro-16-(m-trifluoromethylphenoxy)-17,18,19,20-tetranor-;
2,2-Difluoro-16-(m-chlorophenoxy)-17,18,19,20-tetranor-;
2,2-Difluoro-16-(p-fluorophenoxy)-17,18,19,20-tetranor-;
2,2-Difluoro-16-phenoxy-18,19,20-trinor-;
2,2-Difluoro-16-methyl-16-phenoxy-18,19,20-trinor-;
2,2-Difluoro-16-methyl13,14-didehydro-;
2,2-Difluoro-16,16-dimethyl-13,14-didehydro-;
2,2-Difluoro-16-fluoro-13,14-didehydro-;
2,2-Difluoro-16,16-difluoro-13,14-didehydro-;
2,2-Difluoro-17-phenyl-18,19,20-trinor-13,14-didehydro-;
2,2-Difluoro-17-(m-trifluoromethylphenyl)-18,19,20-trinor-13,14-didehydro-;
2,2-Difluoro-17-(m-chlorophenyl)-18,19,20-trinor-13,14-didehydro-;
2,2-Difluoro-17-(p-fluorophenyl)-18,19,20-trinor-13,14-didehydro-;
2,2-Difluoro-16-methyl-17-phenyl-18,19,20-trinor-13,14-didehydro-;
2,2-Difluoro-16,16-dimethyl-17-phenyl-18,19,20-trinor-13,14-didehydro-;
2,2,16-Trifluoro-17-phenyl-18,19,20-trinor-13,14-didehydro-;
2,2,16,16-Tetrafluoro-17-phenyl-18,19,20-trinor-13,14-didehydro-;
2,2-Difluoro-16-phenyl-17,18,19,20-tetranor-13,14-didehydro-;
2,2-Difluoro-16-(m-trifluoromethylphenyl)-17,18,19,20-tetranor-13,14-didehydro-;
2,2-Difluoro-16-(m-chlorophenyl)-17,18,19,20-tetranor-13,14-didehydro-;
2,2-Difluoro-16-phenyl-18,19,20-trinor-13,14-didehydro-;
2,2-Difluoro-16-methyl-16-phenyl-18,19,20-trinor-13,14-didehydro-;
2,2-Difluoro-16-phenoxy-17,18,19,20-tetranor-13,14-didehydro-;
2,2-Difluoro-16-(m-trifluoromethylphenoxy)-17,18,19,20-tetranor-13,14-didehydro-;
2,2-Difluoro-16-(m-chlorophenoxy)-17,18,19,20-tetranor-13,14-didehydro-;
2,2-Difluoro-16-phenoxy-18,19,20-trinor-13,14-didehydro-;
2,2-Difluoro-16-methyl-16-phenoxy-18,19,20-trinor-13,14-didehydro-;
2,2-Difluoro-13,14-dihydro-;
2,2-Difluoro-16-methyl-13,14-dihydro-;
2,2-Difluoro-16,16-dimethyl-13,14-dihydro-;
2,2,16-Trifluoro-13,14-dihydro-;
2,2,16,16-Tetrafluoro-13,14-dihydro-;

2,2-Difluoro-17-phenyl-18,19,20-trinor-13,14-dihydro-;
2,2-Difluoro-17-(m-trifluoromethylphenyl)-18,19,20-trinor-13,14-dihydro-;
2,2-Difluoro-17-(m-chlorophenyl)-18,19,20-trinor-13,14-dihydro-;
2,2-Difluoro-17-(p-fluorophenyl)-18,19,20-trinor-13,14-dihydro-;
2,2-Difluoro-16-methyl-17-phenyl-18,19,20-trinor-13,14-dihydro-;
2,2-Difluoro-16,16-dimethyl-17-phenyl-18,19,20-trinor-13,14-dihydro-;
2,2,16-Trifluoro-17-phenyl-18,19,20-trinor-13,14-dihydro-;
2,2,16,16-Tetrafluoro-17-phenyl-18,19,20-trinor-13,14-dihydro-;
2,2-Difluoro-16-phenyl-17,18,19,20-tetranor-13,14-dihydro-;
2,2-Difluoro-16-(m-trifluoromethylphenyl)-17,18,19,20-tetranor-13,14-dihydro-;
2,2-Difluoro-16-(m-chlorophenyl)-17,18,19,20-tetranor-13,14-dihydro-;
2,2-Difluoro-16-(p-fluorophenyl)-17,18,19,20-tetranor-13,14-dihydro-;
2,2-Difluoro-16-phenyl-16-phenyl-18,19,20-trinor-13,14-dihydro-;
2,2-Difluoro-16-methyl-16-phenyl-18,19,20-trinor-13,14-dihydro-;
2,2-Difluoro-16-phenoxy-17,18,19,20-tetranor-13,14-dihydro-;
2,2-Difluoro-16-(m-trifluoromethylphenoxy)-17,18,19,20-tetranor-13,14-dihydro-;
2,2-Difluoro-16-(m-chlorophenoxy)-17,18,19,20-tetranor-13,14-dihydro-;
2,2-Difluoro-16-(p-fluorophenoxy)-17,18,19,20-tetranor-13,14-dihydro-;
2,2-Difluoro-16-phenoxy-18,19,20-trinor-13,14-dihydro-;
2,2-Difluoro-16-methyl-16-phenoxy-18,19,20-trinor-13,14-dihydro-;
2,2-Difluoro-13-cis-;
2,2-Difluoro-16-methyl-13-cis-;
2,2-Difluoro-16,16-dimethyl-13-cis-;
2,2,16-Trifluoro-13-cis-;
2,2,16,16,-Tetrafluoro-13-cis-;
2,2-Difluoro-17-phenyl-18,19,20-trinor-13-cis-;
2,2-Difluoro-17-(m-trifluoromethylphenyl)-18,19,20-trinor-13-cis-;
2,2-Difluoro-17-(m-chlorophenyl)-18,19,20-trinor-13-cis-;
2,2-Difluoro-17-(p-fluorophenyl)-18,19,20-trinor-13-cis-;
2,2-Difluoro-16-(methyl-17-phenyl-18,19,20-trinor-13-cis-;
2,2-Difluoro-16,16-dimethyl-17-phenyl-18,19,20-trinor-13-cis-;
2,2,16-Trifluoro-17-phenyl-18,19,20-trinor-13-cis-;
2,2,16,16-Tetrafluoro-17-phenyl-18,19,20-trinor-13-cis-;
2,2-Difluoro-16-phenyl-17,18,19,20-tetranor-13-cis-;
2,2-Difluoro-16-(m-trifluoromethylphenyl)-17,18,19,20-tetranor-13-cis-;
2,2-Difluoro-16-(m-chlorophenyl)-17,18,19,20-tetranor-13-cis-;
2,2-Difluoro-16-(p-fluorophenyl)-17,18,19,20-tetranor-13-cis-;
2,2-Difluoro-16-phenyl-18,19,20-trinor-13-cis-;
2,2-Difluoro-16-methyl-16-phenyl-18,19,20-trinor-13-cis-;
2,2-Difluoro-16-phenoxy-17,18,19,20-tetranor-13-cis-;
2,2-Difluoro-16-(m-trifluoromethylphenoxy)-17,18,19,20-tetranor-13-cis-;
2,2-Difluoro-16-(m-chlorophenoxy)-17,18,19,20-tetranor-13-cis-;
2,2-Difluoro-16-(p-fluorophenoxy)-17,18,19,20-tetranor-13-cis-;
2,2-Difluoro-16-phenoxy-18,19,20-trinor-13-cis-;
2,2-Difluoro-16-methyl-16-phenoxy-18,19,20-trinor-13-cis-;
trans-2,3-Didehydro-;
trans-2,3-Didehydro-15-methyl-;
trans-2,3-Didehydro-16-methyl-;
trans-2,3-Didehydro-16,16-dimethyl-;
trans-2,3-Didehydro-16-fluoro-;
trans-2,3-Didehydro-16,16-difluoro-;
trans-2,3-Didehydro-17-phenyl-18,19,20-trinor-;
trans-2,3-Didehydro-17-(m-trifluoromethylphenyl)-18,19,20-trinor-;
trans-2,3-Didehydro-17-(m-chlorophenyl)-18,19,20-trinor-;
trans-2,3-Didehydro-17-(p-fluorophenyl)-18,19,20-trinor-;
trans-2,3-Didehydro-16-methyl-17-phenyl-18,19,20-trinor-;
trans-2,3-Didehydro-16,16-dimethyl-17-phenyl-18,19,20-trinor-;
trans-2,3-Didehydro-16-fluoro-17-phenyl-18,19,20-trinor-;
trans-2,3-Didehydro-16,16-difluoro-17-phenyl-18,19,20-trinor-;
trans-2,3-Didehydro-16-phenyl-17,18,19,20-tetranor-;
trans-2,3-Didehydro-16-(m-trifluoromethylphenyl)-17,18,19,20-tetranor-;
trans-2,3-Didehydro-16-(m-chlorophenyl)-17,18,19,20-tetranor-;
trans-2,3-Didehydro-16-(p-fluorophenyl)-17,18,19,20-tetranor-;
trans-2,3-Didehydro-16-phenyl-18,19,20-trinor-;
trans-2,3-Didehydro-16-methyl-16-phenyl-18,19,20-trinor-;
trans-2,3-Didehydro-16-phenoxy-17,18,19,20-tetranor-;
trans-2,3-Didehydro-16-(m-trifluoromethylphenoxy)-17,18,19,20-tetranor-;
trans-2,3-Didehydro-16-(m-chlorophenoxy)-17,18,19,20-tetranor-;
trans-2,3-Didehydro-16-(p-fluorophenoxy)-17,18,19,20-tetranor-;
trans-2,3-Didehydro-16-phenoxy-18,19,20-trinor-;
trans-2,3-Didehydro-16-methyl-16-phenoxy-18,19,20-trinor-;
trans-2,3-Didehydro-13,14-didehydro-;
trans-2,3-Didehydro-16-methyl-13,14-didehydro-;
trans-2,3-Didehydro-16,16-dimethyl-13,14-didehydro-;
trans-2,3-Didehydro-16-fluoro-13,14-didehydro-;
trans-2,3-Didehydro-16,16-difluoro-13,14-didehydro-;
trans-2,3-Didehydro-17-phenyl-18,19,20-trinor-13,14-didehydro-;
trans-2,3-Didehydro-17-(m-trifluoromethylphenyl)-18,19,20-trinor-13,14-didehydro-;
trans-2,3-Didehydro-17-(m-chlorophenyl)-18,19,20-trinor-13,14-didehydro-;

trans-2,3-Didehydro-17-(p-fluorophenyl)-18,19,20-trinor-13,14-didehydro-;
trans-2,3-Didehydro-16-methyl-17-phenyl-18,19,20-trinor-13,14-didehydro-;
trans-2,3-Didehydro-16,16-dimethyl-17-phenyl-18,19,20-trinor-13,14-didehydro-;
trans-2,3-Didehydro-16-fluoro-17-phenyl-18,19,20-trinor-13,14-didehydro-;
trans-2,3-Didehydro-16,16-difluoro-17-phenyl-18,19,20-trinor-13,14-didehydro-;
trans-2,3-Didehydro-16-phenyl-17,18,19,20-tetranor-13,14-didehydro-;
trans-2,3-Didehydro-16-(m-trifluoromethylphenyl)-17,18,19,20-tetranor-13,14-didehydro-;
trans-2,3-Didehydro-16-(m-chlorophenyl)-17,18,19,20-tetranor-13,14-didehydro-;
trans-2,3-Didehydro-16-phenyl-18,19,20-trinor-13,14-didehydro-;
trans-2,3-Didehydro-16-methyl-16-phenyl-18,19,20-trinor-13,14-didehydro-;
trans-2,3-Didehydro-16-phenoxy-17,18,19,20-tetranor-13,14-didehydro-;
trans-2,3-Didehydro-16-(m-trifluoromethylphenoxy)-17,18,19,20-tetranor-13,14-didehydro-;
trans-2,3-Didehydro-16-(m-chlorophenoxy)-17,18,19,20-tetranor-13,14-didehydro-;
trans-2,3-Didehydro-16-phenoxy-18,19,20-trinor-13,14-didehydro-;
trans-2,3-Didehydro-16-methyl-16-phenoxy-18,19,20-trinor-13,14-didehydro-;
trans-2,3-Didehydro-13,14-dihydro-;
trans-2,3-Didehydro-16-methyl-13,14-dihydro-;
trans-2,3-Didehydro-16,16-dimethyl-13,14-dihydro-;
trans-2,3-Didehydro-16-fluoro-13,14-dihydro-;
trans-2,3-Didehydro-16,16-difluoro-13,14-dihydro-;
trans-2,3-Didehydro-17-phenyl-18,19,20-trinor-13,14-dihydro-;
trans-2,3-Didehydro-17-(m-trifluoromethylphenyl)-18,19,20-trinor-13,14-dihydro-;
trans-2,3-Didehydro-17-(m-chlorophenyl)-18,19,20-trinor-13,14-dihydro-;
trans-2,3-Didehydro-17-(p-fluorophenyl)-18,19,20-trinor-13,14-dihydro-;
trans-2,3-Didehydro-16-methyl-17-phenyl-18,19,20-trinor-13,14-dihydro-;
trans-2,3-Didehydro-16,16-dimethyl-17-phenyl-18,19,20-trinor-13,14-dihydro-;
trans-2,3-Didehydro-16-fluoro-17-phenyl-18,19,20-trinor-13,14-dihydro-;
trans-2,3-Didehydro-16,16-difluoro-17-phenyl-18,19,20-trinor-13,14-dihydro-;
trans-2,3-Didehydro-16-phenyl-17,18,19,20-tetranor-13,14-dihydro-;
trans-2,3-Didehydro-16-(m-trifluoromethylphenyl)-17,18,19,20-tetranor-13,14-dihydro-;
trans-2,3-Didehydro-16-(m-chlorophenyl)-17,18,19,20-tetranor-13,14-dihydro-;
trans-2,3-Didehydro-16-(p-fluorophenyl)-17,18,19,20-tetranor-13,14-dihydro-;
trans-2,3-Didehydro-16-phenyl-18,19,20-trinor-13,14-dihydro-;
trans-2,3-Didehydro-16-methyl-16-phenyl-18,19,20-trinor-13,14-dihydro-;
trans-2,3-Didehydro-16-phenoxy-17,18,19,20-tetranor-13,14-dihydro-;
trans-2,3-Didehydro-16-(m-trifluoromethylphenoxy)-17,18,19,20-tetranor-13,14-dihydro-;
trans-2,3-Didehydro-16-(m-chlorophenoxy)-17,18,19,20-tetranor-13,14-dihydro-;
trans-2,3-Didehydro-16-(p-fluorophenoxy)-17,18,19,20-tetranor-13,14-dihydro-;
trans-2,3-Didehydro-16-phenoxy-18,19,20-trinor-13,14-dihydro-;
trans-2,3-Didehyro-16-methyl-16-phenoxy-18,19,20-trinor-13,14-dihydro-;
trans-2,3-Didehydro-13-cis-;
trans-2,3-Didehydro-16-methyl-13-cis-;
trans-2,3-Didehydro-16,16-dimethyl-13-cis-;
trans-2,3-Didehydro-16-fluoro-13-cis-;
trans-2,3-Didehydro-16,16-difluoro-13-cis-;
trans-2,3-Didehydro-17-phenyl-18,19,20-trinor-13-cis-;
trans-2,3-Didehydro-17-(m-trifluoromethylphenyl)-18,19,20-trinor-13-cis-;
trans-2,3-Didehydro-17-(m-chlorophenyl)-18,19,20-trinor-13-cis-;
trans-2,3-Didehydro-17-(p-fluorophenyl)-18,19,20-trinor-13-cis-;
trans-2,3-Didehydro-16-methyl-17-phenyl-18,19,20-trinor-13-cis-;
trans-2,3-Didehydro-16,16-dimethyl-17-phenyl-18,19,20-trinor-13-cis-;
trans-2,3-Didehydro-16-fluoro-17-phenyl-18,19,20-trinor-13-cis-;
trans-2,3-Didehydro-16,16-difluoro-17-phenyl-18,19,20-trinor-13-cis-;
trans-2,3-Didehydro-16-phenyl-17,18,19,20-tetranor-13,-cis-;
trans-2,3-Didehydro-16-(m-trifluoromethylphenyl)-17,18,19,20-tetranor-13-cis-;
trans-2,3-Didehydro-16-(m-chlorophenyl)-17,18,19,20-tetranor-13-cis-;
trans-2,3-Didehydro-16-(p-fluorophenyl)-17,18,19,20-tetranor-13-cis-;
trans-2,3-Didehydro-16-phenyl-18,19,20-trinor-13-cis-;
trans-2,3-Didehydro-16-methyl-16-phenyl-18,19,20-trinor-13-cis-;
trans-2,3-Didehydro-16-phenoxy-17,18,19,20-tetranor-13-cis-;
trans-2,3-Didehydro-16-(m-trifluoromethylphenoxy)-17,18,19,20-tetranor-13-cis-;
trans-2,3-Didehydro-16-(m-chlorophenoxy)-17,18,19,20-tetranor-13cis-;
trans-2,3-Didehydro-16-(p-fluorophenoxy)-17,18,19,20-tetranor-13-cis-;
trans-2,3-Didehydro-16-phenoxy-18,19,20-trinor-13-cis-;
trans-2,3-Didehydro-16-methyl-16-phenoxy-18,19,20-trinor-13-cis-;
and their corresponding 11-deoxy-PGF$_1$ and 11-deoxy-11-hydroxymethyl-PGF$_1$ analogs.

Further, following procedures described above there are prepared the corresponding hydrochloride salts of each of the above compounds and the pharmacologically acceptable cations of compounds above in free acid form.

EXAMPLE 8

9-deoxy-9a,5-nitrilo-PGF$_1$, methyl ester

A. cis-4,5-didehydro-PGF$_1$, methyl ester (2.0 gms) is dissolved in dimethylformamide (6 ml) and cooled to 0° C. is combined with t-butyldimethylsilyl chloride (1.72 gms), imidazole (1.55 gms) and dimethylformamide (6 ml). Resulting mixture is stirred at 0° C. for 2 hrs and thereafter stirred an additional 2 hrs at room temperature. When thin layer chromatographic analysis indicates the reaction to be complete, the reaction mixture is poured into brine, extracted with hexane, and the hexane extracts washed with brine and dried over magnesium sulfate. Concentration under reduced pressure and chromatography of the resulting residue on 200 gms of silica gel eluting with 15% ethyl acetate and hexane yields 2,3 g. of cis-4,5-dehydro-PGF$_1\alpha$, methyl ester, 11,15-bis(t-butyldimethylsilyl ether).

B. The reaction product of part A (2,3 gms), triphenylphosphine (2.02 gms) and benzoic acid (942 mg) in tetrahydrofuran (35 ml) is cooled to 0° C. and added to a mixture of diethyl azodicarboxylate in tetrahydrofuran (5 ml) over 5 min. Stirring is continued for 30 min. at 0° C. and thereafter the tetrahydrofuran is removed under reduced pressure. The resulting residue is then dissolved in 100 ml of a mixture of ethyl acetate and hexane (1:9) and triphenylphosphineoxide (10 mg) is added. Stirring is continued for 1 hr and the resulting mixture filtered and the solids washed with ethyl acetate and hexane. The filtrate is then diluted to a volume of 300 ml with hexane, washed with sodium bicarbonate and brine, dried over magnesium sulfate, and concentrated to a residue. This residue is then chromatographed on 200 gm of silica gel packed with ethyl acetate in hexane (1:19) and eluted with ethyl acetate in hexane (1:19), yielding 1.969 gm of cis-4,5-didehydro-PGF$_1\beta$, methyl ester, 9-benzoate, 7,15-bis(t-butyldimethylsilyl ether).

C. The reaction product of part B (1.96 gms) is dissolved in 10 ml of methanol and the resulting mixture added to 25% sodium methoxide in methanol (1.5 ml) and 2 ml of tetrahydrofuran under a nitrogen atmosphere. The mixture is stirred at ambient temperature for 4 hrs and then poured into a mixture of ice brine and ethyl acetate in hexane (1:4). Extraction with ethyl acetate and hexane (1:4), washing the organic phase with sodium bicarbonate in brine, drying over magnesium sulfate and concentrating under reduced pressure yields 1.98 gms of crude cis-4,5-didehydro-PGF$_1\beta$, methyl ester, 11,15-bis(t-butyldimethylsilyl ether).

D. A mixture of the reaction product of part C, pyridine (10 ml), and p-toluenesulfonyl chloride (1.06 gm) is stirred overnight at ambient temperature until thin layer chromatographic analysis indicates the reaction to be complete. The resulting mixture is then cooled to 0° C. and water (10 ml) is added with stirring for 10 min. The resulting mixture is then poured into an ice brine mixture and extracted with ethyl acetate in hexane (1:9). The organic extracts are then washed with water, dilute sodium bisulfate, sodium bicarbonate and brine; dried over magnesium sulfate, and concentrated under reduced pressure to yield 2.5 gm of crude cis-4,5-didehydro-PGF$_1\beta$, methyl ester, 9-(p-toluenesulfonate), 11,15-bis(t-butyldimethylsilyl ether).

E. The reaction product of part D, tetrahydrofuran (20 ml), water (20 ml), and acetic acid (60 ml) is stirred at ambient temperature for 48 hrs whereupon the resulting mixture is poured into brine and water (1:1) and extracted with ethyl acetate and hexane (1:1). The organic layers are then cautiously washed with sodium bicarbonate until basic pH's are obtained and thereafter washing continues with brine, followed by drying with magnesium sulfate and concentration under reduced pressure. The resulting crude product is then chromatographed on 250 gm of silica gel packed with ethyl acetate and hexane (1:1) and eluted with 60-100% ethyl acetate in hexane, yielding 1.15 gms of pure cis-4,5-didehydro-PGF$_1\beta$, methyl ester, 9-(p-toluenesulfonate).

F. The reaction product of part E (1.115 gms) hexamethylphosforamide (60 ml) and sodium azide (6 gms) are stirred under a nitrogen atmosphere at 40° C. for 2 hrs. The mixture is then cooled, poured into a mixture of ice, brine, water, and diethyl ether and thereafter extracted with diethyl ether. The organic layers are then washed with water and brine, dried over magnesium sulfate, and concentrated under reduced pressure to yield 1.00 gm of 9-deoxy-9α-azido-cis-4,5-didehydro-PGF$_1\alpha$, methyl ester.

G. The reaction product of part F (500 mg) in 50 ml of ethyl acetate is heated to 80° C. for 62 hrs. Thereupon the residue is concentrated under reduced pressure and chromatographed on 75 gm of silica gel packed and eluted with 20% methanol and ethyl acetate. There are thereupon obtained 250-300 mg of pure title product. A characteristic infrared absorption for —C=N— is observed at 1660 cm$^{-1}$.

I claim:

1. A prostacyclin analog of the formula

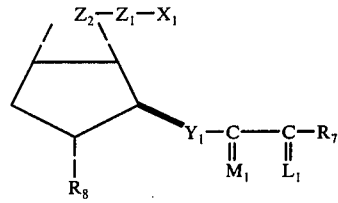

wherein
$Z_2$ is

 (1)

 (2)

 (3)

wherein
$R_2$ is alkyl of one to 4 carbon atoms, inclusive, or alkylcarbonyl of one to 4 carbon atoms, inclusive;
wherein $Z_1$ is
(1) —(CH$_2$)$_g$—CH$_2$—CH$_2$—,
(2) —(CH$_2$)$_g$—CH$_2$—CF$_2$—, or
(3) trans—(CH$_2$)$_g$—CH=CH—,
wherein
g is the integer zero, one, or 2;
wherein
R$_8$ is hydrogen, hydroxy, or hydroxymethyl;
wherein
Y$_1$ is
(1) trans—CH=CH—,
(2) cis—CH=CH—,
(3) —CH$_2$CH$_2$—,
(4) trans—CH=C(Hal)—, or
(5) —C≡C— wherein
Hal is chloro or bromo;
wherein
M₁ is

 
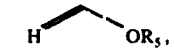 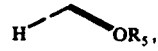
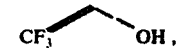 
 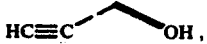
 

wherein
$R_5$ is hydrogen or alkyl with one to 4 carbon atoms, inclusive.
wherein
$L_1$ is

R₃ R₄, R₃ R₄, or a mixture of

R₃ R₄ and R₃ R₄, wherein
$R_3$ and $R_4$ are hydrogen, methyl, or fluoro, being the same or different, with the proviso that one of $R_3$ and $R_4$ is fluoro only when the other is hydrogen or fluoro;
wherein
$X_1$ is
(1) —COOR₁ wherein $R_1$ is hydrogen; alkyl of one to 12 carbon atoms, inclusive; cycloalkyl of 3 to 10 carbon atoms, inclusive, aralkyl of 7 to 12 carbon atoms, inclusive; phenyl; phenyl substituted witth one, two, or three chloro or alkyl of one to 3 carbon atoms; phenyl substituted in the para position by $$-NH-\overset{O}{\underset{\|}{C}}R_{25} \qquad (a)$$

$$-O-\overset{O}{\underset{\|}{C}}-R_{26} \qquad (b)$$

$$-O-\overset{O}{\underset{\|}{C}}-\!\!\!\bigcirc\!\!\!-R_{27}, \text{ or} \qquad (c)$$

$$-CH=N-NH\overset{O}{\underset{\|}{C}}-NH_2 \qquad (d)$$

wherein $R_{25}$ is methyl, phenyl, acetamidophenyl, benzamidophenyl, or —NH₂; $R_{26}$ is methyl, phenyl, —NH₂, or methoxy; and $R_{27}$ is hydrogen or acetamido, inclusive; or a pharmacologically acceptable cation;
(2) —CH₂OH; or
(3) —COL₄, wherein $L_4$ is (a) amido of the formula —NR₂₁R₂₂, wherein $R_{21}$ and $R_{22}$ are
(i) hydrogen;
(ii) alkyl of one to 12 carbon atoms, inclusive;
(iii) cycloalkyl of 3 to 10 carbon atoms, inclusive;
(iv) aralkyl of 7 to 12 carbon atoms, inclusive;
(v) phenyl;
(vi) phenyl substituted with one, 2, or 3 chloro, alkyl of one to 3 carbon atoms, inclusive, hydroxy of one to 3 carbon atoms, inclusive, carboxy, alkoxycarbonyl of one to 4 carbon atoms, inclusive, or nitro;
(vii) carboxyalkyl of one to 4 carbon atoms, inclusive;
(viii) carbamoylalkyl of one to 4 carbon atoms, inclusive;
(ix) cyanoalkyl of one to 4 carbon atoms, inclusive;
(x) acetylalkyl of one to 4 carbon atoms, inclusive;
(xi) benzoylalkyl of one to 4 carbon atoms, inclusive;
(xii) benzoylalkyl substituted by one, 2, or 3 chloro, alkyl of one to 3 carbon atoms, inclusive, hydroxy, alkoxy of one to 3 carbon atoms, inclusive, carboxy, alkoxycarbonyl of one to 4 carbon atoms, inclusive, or nitro;
(xvii) hydroxyalkyl of one to 4 carbon atoms, inclusive;
(xviii) dihydroxyalkyl of one to 4 carbon atoms; or
(xix) trihydroxyalkyl of one to 4 carbon atoms; with the further proviso that not more than one of $R_{21}$ and $R_{22}$ is other than hydrogen or alkyl;
(b) carbonylamido of the formula —NR₂₃COR₂₁, wherein $R_{23}$ is hydrogen or alkyl of one to 4 carbon atoms and $R_{21}$ is as defined above; or
(c) sulphonylamido of the formula —NR₂₃SO₂R₂₁, wherein $R_{21}$ and $R_{23}$ are as defined above;
(d) hydrazino of the formula —NR₂₃R₂₄, wherein $R_{24}$ is amido of the formula —NR₂₁R₂₂, as defined above;
wherein
$R_7$ is
(1) —(CH₂)ₘ—CH₃, $$-(CH_2)_m-CH_3, \qquad (1)$$

$$-(CH_2)_h-\!\!\!\bigcirc\!\!\!-(T)_s, \text{ or} \qquad (2)$$

$$-O-\!\!\!\bigcirc\!\!\!-(T)_s \qquad (3)$$

wherein $m$ is the integer one to 5, inclusive, $h$ is the integer zero to 3, inclusive; s is the integer zero, one, 2, or 3, and T is chloro, fluoro, trifluoromethyl, alkyl of one to 3 carbon atoms, inclusive, or alkoxy of one to 3 carbon atoms, inclusive, or alkoxy of one to 3 carbon atoms, inclusive, or with the proviso that not more than two T's are other than alkyl; and the pharmacologically acceptable acid addition salts thereof when $R_2$ is not alkylcarbonyl and $R_1$ is not a pharmacologically acceptable cation.

2. A prostacyclin analog according to claim 1, wherein $R_8$ s hydroxymethyl.

3. 9,11-Dideoxy-11α-hydroxymethyl-9α,6-nitrilo-$PGF_1$, a prostacyclin analog according to claim 2.

4. A prostacyclin analog according to claim 1, wherein $R_8$ is hydrogen.

5. 9,11-Dideoxy-9α,6-nitrilo-$PGF_1$, a prostacyclin analog according to claim 4.

6. A prostacyclin analog according to claim 1, wherein $R_8$ is hydroxy.

7. A prostacyclin analog according to claim 6, wherein $Z_2$ is

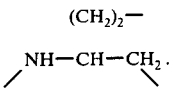

8. (6R)- or (6S)-9-deoxy-6,9α-imino-$PGF_1$, a prostacyclin analog according to claim 7.

9. A prostacyclin analog according to claim 6, wherein $Z_2$ is

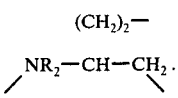

10. (6R)-N-methyl-9-deoxy-6,9α-imino-$PGF_1$, a prostacyclin analog according to claim 9.

11. (6R)-N-acetyl-9-deoxy-6,9α-imino-$PGF_1$, a prostacyclin analog according to claim 9.

12. (6S)-N-methyl-9-deoxy-6,9α-imino-$PGF_1$, a prostacyclin analog according to claim 9.

13. (6S)-N-acetyl-9-deoxy-6,9α-imino-$PGF_1$, a prostacyclin analog according to claim 9.

14. A prostacyclin analog according to claim 6, wherein $Z_2$ is

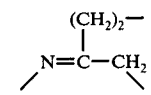

15. A prostacyclin analog according to claim 14, wherein $Y_1$ is cis—CH=CH—.

16. 9-Deoxy-9α,6-nitrilo-cis-13-$PGF_1$, a prostacyclin analog according to claim 15.

17. A prostacyclin analog according to claim 14, wherein $Y_1$ is —C≡C—.

18. 9-Deoxy-9α,6-nitrilo-13,14-didehydro-$PGF_1$, a prostacyclin analog according to claim 17.

19. A prostacyclin analog according to claim 14, wherein $Y_1$ is trans—CH=C(Hal)—.

20. 9-Deoxy-9α,6-nitrilo-14-chloro-$PGF_1$, a prostacyclin analog according to claim 19.

21. A prostacyclin analog according to claim 14, wherein $Y_1$ is —$CH_2CH_2$—.

22. 9-Deoxy-9α,6-nitrilo-13,14-dihydro-$PGF_1$, a prostacyclin analog according to claim 21.

23. A prostacyclin analog according to claim 14, wherein $Y_1$ is trans—CH=CH—.

24. A prostacyclin analog according to claim 23, wherein $Z_1$ is —$(CH_2)_g$—$CH_2$—$CF_2$.

25. 2,2-Difluoro-9-deoxy-9α,6-nitrilo-15-methyl-$PGF_1$, a prostacyclin analog according to claim 24.

26. A prostacyclin analog according to claim 23, wherein $Z_1$ is trans—$(CH_2)_g$—CH=CH—.

27. Trans-2,3-didehydro-9-deoxy-9α,6-nitrilo-$PGF_1$, a prostacyclin analog according to claim 26.

28. A prostacyclin analog according to claim 23, wherein $Z_1$ is —$(CH_2)_g$—$CH_2$—$CH_2$—.

29. A prostacyclin analog according to clam 28, wherein g is zero.

30. A prostacyclin analog according to clam 29, wherein $R_7$ is

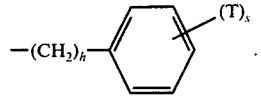

31. 9-Deoxy-9α,6-nitrilo-17-phenyl-18,19,20-trinor-$PGF_1$, a prostacyclin analog according to claim 30.

32. A prostacyclin analog according to claim 29, wherein $R_7$ is

33. 9-Deoxy-9α,6-nitrilo-16-phenoxy-17,18,19,20-tetranor-$PGF_1$, a prostacyclin analog according to claim 32.

34. A prostacyclin analog according to claim 29, wherein $R_7$ is —$(CH_2)_m$—$CH_3$—.

35. A prostacyclin analog according to claim 34, wherein m is 3.

36. A prostacyclin analog according to claim 35, wherein $X_1$ is —$COL_4$.

37. 9-Deoxy-9α,6-nitrilo-$PGF_1$, amide, a prostacyclin analog according to claim 36.

38. A prostacyclin analog according to claim 35, wherein $X_1$ is $CH_2OH$—.

39. 2-Decarboxy-2-hydroxymethyl-9-deoxy-9α,6-nitrilo-$PGF_1$, a prostacyclin analog according to claim 38.

40. A prostacyclin analog according to claim 35, wherein $X_1$ is —$COOR_1$.

41. A prostacyclin analog according to claim 40, wherein $R_5$ is methyl.

42. 9-Deoxy-9α,6-nitrilo-15-methyl-$PGF_1$, a prostacyclin analog according to claim 41.

43. A prostacyclin analog according to claim 40, wherein $R_5$ is hydrogen.

44. A prostacyclin analog according to claim 43, wherein at least one of $R_3$ and $R_4$ is fluoro.

45. 9-Deoxy-9α,6-nitrilo-16,16-difluoro-$PGF_1$, a prostacyclin analog according to claim 44.

46. A prostacyclin analog according to claim 43, wherein at least one of $R_3$ and $R_4$ is methyl.

47. 9-Deoxy-9α,6-nitrilo-16,16-dimethyl-$PGF_1$, a prostacyclin analog according to claim 46.

48. A prostacyclin analog according to claim 43, wherein $R_3$ and $R_4$ are both hydrogen.

49. 9-Deoxy-9α,6-nitrilo-$PGF_1$, methyl ester, a prostacyclin analog according to claim 48.

50. 9-Deoxy-9α,6-nitrilo-$PGF_1$, tris(hydroxymethyl)amino methane salt, a prostacyclin analog according to claim 48.

51. 9-Deoxy-9α,6-nitrilo-$PGF_1$, hydrochloride, a prostacyclin analog according to claim 48.

52. 9-Deoxy-9α,6-nitrilo-$PGF_1$, a prostacyclin analog according to claim 48.

* * * * *

UNITED STATES PATENT OFFICE
CERTIFICATE OF CORRECTION

Patent No. 4,097,489                    Dated 27 June 1978

Inventor(s) Gordon L. Bundy

It is certified that error appears in the above-identified patent and that said Letters Patent are hereby corrected as shown below:

Column 1, lines 38-43, the formula should appear as follows:

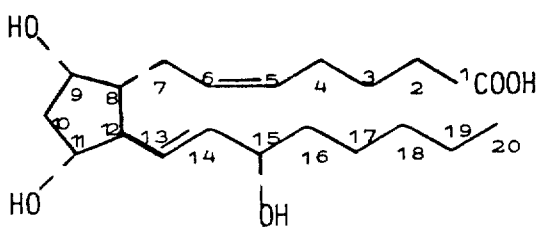

Column 4, line 51, "amido" should read -- amino --;
Column 5, line 17, "cycloamido" should read -- cycloamino --;
Column 5, line 43, "carbonylamido" should read -- carbonylamino --; line 47, "sulphonylamido" should read -- sulfonylamino --; line 50, "amido" should read -- amino --; line 51, "cycloamido" should read -- cycloamino --;
Column 9, line 23, "cyclopenyl," should read -- cyclopentyl, --;
Column 10, line 9, "alkylamido" should read -- alkylamino --; line 19-20, "cycloalkylamido" should read -- cycloalkylamino --; line 30, "aralkylamido" should read -- aralkylamino --; line 34, "phenylamido" should read -- phenylamino --; line 38, "p-methylanalide" should read -- p-methylanilide --; line 41-42, "carboxyakylamido" should read -- carboxyalkylamino --; line 44, "carbamoylakylamido" should read -- carbamoylalkylamino --; line 47, "cyanoalkylamido" should read -- cyanoalkylamino --; line 49-50, "acetylalkylamido" should read -- acetylalkylamino --; line 52, "benzoylalkylamido" should read -- benzoylalkylamino --; line 55, "benzoylalkylamido" should read -- benzoylalkylamino --;
Column 11, line 33, "pryidylamido" should read -- pyridylamino --; line 35, "pyridylamido" should read -- pyridylamino --; line 38, "pyridylalkylamido" should read -- pyridylalkylamino --; line 44-45, "pyridylalkylamido" should read -- pyridylalkylamino --; line 56, "hydroxyalkyl" should read -- hydroxyalkylamino --; line 62, "dihydroxyalkylamido" should read -- dihydroxyalkylamino --;

UNITED STATES PATENT OFFICE
CERTIFICATE OF CORRECTION

Patent No. 4,097,489      Dated 27 June 1978

Inventor(s) Gordon L. Bundy

It is certified that error appears in the above-identified patent and that said Letters Patent are hereby corrected as shown below:

Column 12, line 4, "α,γ-dihydroxybutylamide" should read -- β,γ-dihydroxybutylamide --; line 11, "cycloamido" should read -- cycloamino --; line 16, "carbonylamido" should read -- carbonylamino --; line 19, "sulfonylamido" should read -- sulfonylamino --;

Column 27, line 33, "11,151-bis(tetrahydropyranyl" should read -- 11,15-bis(tetrahydropyranyl --;

Column 29, line 14, "Rhd 3 and $R_41$ of the $L_1$ moiety" should read -- $R_3$ and $R_4$ of the $L_1$ moiety --; line 8, "$Y_1$ is trans-$CH_1CH$-," should read -- $Y_1$ is trans-CH=CH-, --;

Column 30, line 13, "and 970 $cm^{-1}$." should read -- and 970 $cm^{-1}$. For the (6R) isomer the melting point is 186-188° C. --

Column 31, lines 10-15,

" [structure: $CH_3C(=O)$, $CH_2-$, N, $CH-CH_2$] " should read -- [structure: $CH_3C(=O)$, $CH_2-$, N-$CH-CH_2$] --

Column 39, line 9, "2,3 g." should read -- 2.3 g. --; line 11, "(2,3 gms)," should read -- (2.3 gm), --;

Column 40, line 68, "(5) -C=C-" should read -- (5) -C≡C- --;

Column 42, line 1, "amido" should read -- amino --; line 37, "carbonylamido" should read -- carbonylamino --; line 40, "sulphonylamido" should read -- sulfonylamino --; line 45, "amido" should read -- amino --;

UNITED STATES PATENT OFFICE
CERTIFICATE OF CORRECTION

Patent No. 4,097,489   Dated  27 June 1978

Inventor(s)  Gordon L. Bundy

It is certified that error appears in the above-identified patent and that said Letters Patent are hereby corrected as shown below:

Column 43, line 6, "wherein $R_B$ 8s hydroxy" should read -- wherein $R_B$ is hydroxy --; lines 17-21, $$\begin{array}{c} \phantom{NH-}(CH_2)_2- \\ \diagup NH-CH-CH_2 \diagdown \end{array} \quad \text{should read} \quad \begin{array}{c} \phantom{NH-}(CH_2)_2- \\ \diagup NH-CH-CH_2 \diagdown \end{array} \quad -- \;;$$

lines 28-32, $$\begin{array}{c} \phantom{NR_2-}(CH_2)_2- \\ \diagup NR_2-CH-CH_2 \diagdown \end{array} \quad \text{should read} \quad \begin{array}{c} \phantom{NR_2-}(CH_2)_2- \\ \diagup NR_2-CH-CH_2 \diagdown \end{array} \quad -- \;;$$

line 54, "-C=C-" should read -- -C≡C- --.

Signed and Sealed this

*Seventh* Day of *September 1982*

[SEAL]

*Attest:*

*Attesting Officer*

GERALD J. MOSSINGHOFF
*Commissioner of Patents and Trademarks*